(12) United States Patent
Pensiero et al.

(10) Patent No.: US 6,329,199 B1
(45) Date of Patent: *Dec. 11, 2001

(54) RETROVIRAL VECTORS PRODUCED BY PRODUCER CELL LINES RESISTANT TO LYSIS BY HUMAN SERUM

(76) Inventors: Michael Pensiero, 20910 Beallsville Rd., Dickerson, MD (US) 20842; Mary K. L. Collins, 73 Beak Street, London W1R 3LN (GB); Francois-Loic Cosset, 48 Napier Court Ranleagh Gardens, London SW6 3UU (GB); Yasuhiro Takeuchi, 81 Smeaton Road, London SW18 5JJ (GB); Robin A. Weiss, 25 Cyprus Avenue, London N3 1SS (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/374,746

(22) Filed: Aug. 13, 1999

Related U.S. Application Data

(63) Continuation of application No. 08/516,163, filed on Aug. 17, 1995, now Pat. No. 5,952,225, which is a continuation-in-part of application No. 08/451,215, filed on May 26, 1995, now abandoned, which is a continuation-in-part of application No. 08/291,765, filed on Aug. 17, 1994, now abandoned.

(51) Int. Cl.[7] ............................. C12N 15/867; C12N 5/10; C12N 15/64; C07H 21/04
(52) U.S. Cl. .................. 435/320.1; 435/325; 435/366; 435/368; 435/369; 435/371; 435/455; 435/456; 435/357; 435/363; 435/352; 536/23.1; 536/23.72; 536/24.1
(58) Field of Search ...................... 435/325, 366, 435/368, 369, 371, 320.1, 5, 6, 7.1, 455, 456, 357, 363, 352; 424/93.2, 93.6, 93.1; 536/23.1, 23.72, 24.1

(56) References Cited

U.S. PATENT DOCUMENTS

| | | | |
|---|---|---|---|
| 5,470,726 | * 11/1995 | Miller et al. | 435/465 |
| 5,591,624 | * 1/1997 | Barber et al. | 435/366 |
| 5,952,225 | * 9/1999 | Pensiero et al. | 435/352 |

OTHER PUBLICATIONS

Orkin et al., "Report and Recommendations of the Panel to Assess the NIH Investment in Research on Gene Therapy" Dec. 1995.*
Welsh et al., Nature, vol. 257, pp. 612–614, Oct. 1975.*
Takeuchi et al., Virology, vol. 186, pp. 792–794, 1992.*
Anderson, Nature, vol. 392, pp. 25–30, Apr. 1998.*
Verma et al., Nature, vol. 389, pp. 239–242, Sep. 1997.*

* cited by examiner

*Primary Examiner*—David Guzo
(74) *Attorney, Agent, or Firm*—Geoffrey M. Karny

(57) ABSTRACT

Retroviral vectors which are resistant to inactivation by human serum. The retroviral vectors are produced in a cell line which is resistant to lysis by human serum, such cell lines including the HOS, Mv-1-Lu, HT1080, TE671, and human 293 cell lines, as well as cell lines derived therefrom. Such retroviral vectors are especially useful as in vivo gene delivery vehicles.

8 Claims, 15 Drawing Sheets

SEQUENCE OF THE MULTIPLE CLONING SITE IN THE pGI PLASMID

| 1/2 EcoRI | NotI | SnaBI | SalI | BamHI | XhoI | HindIII | ApaI |
|---|---|---|---|---|---|---|---|
| AATTC | GCGGCCGC | TACGTA | GTCGTA | GGATCC | CTCGAG | AAGCTT | GGGCCC |
| G | CGCCGGCG | ATGCAT | ATGCAT | CCTAGG | GAGCTC | TTCGAA | CCCGGG |

1/2ClaI

AT

TAGC

FIG.6

RETROVIRAL VECTORS PRODUCED BY PRODUCER CELL LINES RESISTANT TO LYSIS BY HUMAN SERUM

This is a Continuation of Application Ser. No. 08/516,163 filed Aug. 17, 1995, now U.S. Pat. No. 5,952,225, which is a continuation-in-part of Application Ser. No. 08/451,215, filed May 26, 1995, abandoned, and is a continuation-in-part of Application Ser. No. 08/291,765, filed Aug. 17, 1994, abandoned, the disclosures of which are incorporated herein by reference.

This invention relates to retroviral vectors which are resistant to inactivation by human serum. More particularly, this application relates to retroviral vectors generated from cells which are resistant to lysis by human serum. In another aspect, this invention relates to gene therapy using such vectors.

BACKGROUND OF THE INVENTION

Retroviruses have been and are being used currently as gene delivery vehicles for introducing desired genes into cells, and are being used in a number of gene therapy trials. (Miller, Nature, Vol. 375, pgs. 455–460 (1992)). Cornetta, et al., Progress in Nucleic Acid Research and Molecular Biology, Vol. 36, pgs. 311–322 (1990) and Cornetta, et al., Human Gene Therapy, Vol. 1, pgs. 15–30 (1990) teach the intravenous infusion into monkeys of an amphotropic murine leukemia retrovirus which includes the human ADA gene. Clinical illness in the monkeys was not observed after administration of the retrovirus. The retroviruses were cleared rapidly from the circulation, and such clearance was mediated in part by complement, which inactivates the virus.

In some trials, direct gene delivery to cells in vivo is being undertaken; for example, the delivery of the Herpes Simplex Virus thymidine kinase gene by recombinant retroviruses to tumors. (Oldfield, et al., Human Gene Therapy, Vol. 4, pgs. 39–69 (1993)). For these trials, murine leukemia virus amphotropic strain (MLV-A) packaging cells, constructed in murine NIH 3T3 cells, are being used to produce recombinant retroviruses.

Murine leukemia viruses produced by NIH3T3 cells, however, can be inactivated rapidly by human serum. Such inactivation is a result of activation of the complement cascade.

The inhibition of infectivity of C-type retroviruses first was demonstrated in reports that four strains of murine leukemia viruses (MLV), and Moloney Sarcoma Virus (MSV) pseudotypes with the envelope specificity of gibbon ape leukemia virus (GALV), or simian sarcoma associated virus (SSAV), were inactivated by fresh, but not heated human serum. (Welsh, et al., Nature, Vol. 257, pgs. 612–614 (1975); Welsh, et al., Virology, Vol. 74, pgs. 432–440 (1976).) Lysis of these viruses, as well as lysis of feline leukemia virus (FeLV), the cat endogenous virus RD114, simian sarcoma associated virus (SSAV), the baboon endogenous virus M28 (BaEV) and the D-type virus Mason-Pfizer monkey virus (MPMV) by human serum was demonstrated by the release of reverse transcriptase activity from virions. (Welsh, et al., 1975; Welsh, et al., 1976; Sherwin, et al., Int. J. Cancer, Vol. 21, pgs. 6–11 (1978).) Complement depleted, or deficient human sera failed to cause viral lysis, and complement consumption was observed when viruses were added to human serum. (Welsh, et al., 1975). Murine leukemia viruses were shown to be lysed following direct, antibody independent triggering of the C1q component to MLV virions. (Cooper, et al., J. Exp. Med., Vol. 144, pgs. 970–984 (1976).) An isolated 15 Kda virion protein with a pI of 7.5, proposed to be the p15E transmembrane protein, was shown to trigger complement. (Bartholomew, et al., J. Exp. Med., Vol. 147, pgs. 844–853 (1978).) Retroviruses made by murine cells, however, were found to be inactivated by human serum mainly by recognition of sugar epitopes, Gal (1–3) Gal epitopes, by natural antibodies (Takeuchi, et al., unpublished data).

BRIEF DESCRIPTION OF THE DRAWINGS

The invention will now be described with respect to the drawings, wherein:

FIG. 6 is the sequence (SEQ ID No:1) of the multiple cloning site in plasmid pG1;

SUMMARY OF THE INVENTION

Figure 1A:
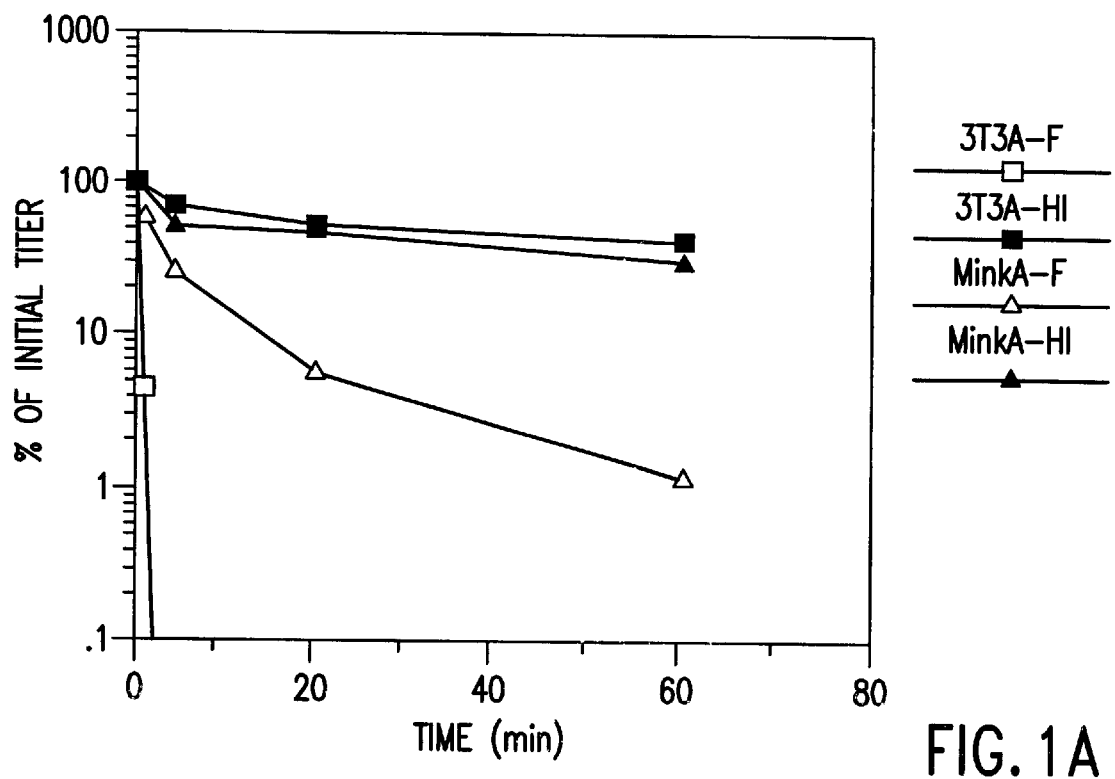
FIGS. 1A and 1B are graphs of the time course of virus inactivation by fresh human serum of MLV-A and RD114 viruses generated from NIH3T3 and mink Mv-1-Lu cells.

Applicants have discovered that when retroviral vectors are produced from a cell line which is resistant to lysis by human serum, such retroviral vectors may be resistant to complement inactivation by human serum, and that such complement resistance is not dependent necessarily upon the envelope employed, even when the envelope is from a murine Type C amphotropic retrovirus.

Thus, the present invention is directed to retroviral vectors which have been produced by a cell line which is resistant to lysis by human serum. The present invention also is directed to gene therapy employing such retroviral vectors, wherein such retroviral vectors contain at least one polynucleotide encoding a therapeutic agent.

DETAILED DESCRIPTION OF THE INVENTION

In accordance with an aspect of the present invention, there is provided a retroviral vector resistant to inactivation by human serum. The retroviral vector has been produced in a cell line which is resistant to lysis by human serum.

Cell lines which are resistant to lysis by human serum include, but are not limited to, HOS, TE671, HT1080, Mv-1-Lu, and a human 293 cell line, or cell lines dervied from the HOS, TE671, HT1080, Mv-1-Lu, or human 293 cell lines.

The term "cell line derived from the HOS, TE671, HT1080, Mv-1-Lu, or human 293 cell lines," as used herein, means a cell line formed by transfecting one of the above-mentioned cell lines with one or more expression vehicles (e.g., plasmid vectors or retroviral vectors or retroviral vector genomes) including polynucleotides encoding various gag, pol, and env proteins. The gag and pol retroviral proteins may be obtained from any retrovirus, including, but not limited to, Moloney Murine Leukemia Virus, Rous Sarcoma Virus, RD114, BaEV, GALV, SSAV, FeLV-B, human immunodeficiency virus, and avian leukosis virus. Alternatively, the gag/pol proteins may be modified or chimeric gag/pol constructs. The envelope may be an amphotropic envelope, an ecotropic envelope, or a xenotropic envelope, or may be an envelope including amphotropic and ecotropic portions. The envelope may be obtained from any retrovirus, including, but not limited to, Moloney Murine Leukemia Virus, Rous Sarcoma Virus, RD114, BaEV, GALV, SSAV, FeLV-B, amphotropic murine leukemia viruses (MLV-A), human immunodeficiency virus, avian leukosis virus and NZB virus. Alternatively, the env proteins may be modified or chimeric env constructs, or may be obtained from non-retroviruses, such as vesicular stomatitis virus and HVJ virus. Such cells also may include other polynucleotides such as, for example, polynucleotides encoding selectable markers.

Applicants have found unexpectedly that retroviruses, including retroviruses including an amphotropic envelope and murine leukemia virus based retroviruses, produced in cell lines which are resistant to lysis by human serum, may be resistant to inactivation (in particular, complement inactivation) by human serum. Thus, such retroviruses are suitable for in vivo administration to an animal host in gene therapy procedures.

The retroviral vectors, in one embodiment, may be produced by transfecting the cells with a retroviral plasmid vector as described hereinbelow. Alternatively, the retroviral vectors may be produced by infecting the cells with a retroviral vector from another packaging cell. The cells also are provided with the retroviral packaging function. The packaging function may be provided by a replication competent retrovirus, or may be provided by a transient system which includes one or more expression vehicles (e.g., plasmid vectors) including polynucleotides encoding the gag, pol, and env proteins. Such functions also may be provided by transfecting stably the cell line with one or more expression vehicles (e.g., plasmid vectors) including polynucleotides encoding the gag, pol, and env proteins.

The term "polynucleotide" as used herein means a polymeric form of nucleotides of any length, and includes ribonucleotides and deoxyribonucleotides. Such term also includes single- and double-stranded DNA, as well as single- and double-stranded RNA. The term also includes such as methylated or capped polynucleotides.

As used herein, the term "retroviral plasmid vector" means a plasmid which includes all or part of a retroviral genome including 5' and 3' retroviral long-term repeat (LTR) sequences, a packaging signal (ψ), and may include one or more polynucleotides encoding a protein(s) or polypeptide (s) of interest, such as a therapeutic agent or a selectable marker. The term "therapeutic" is used in a generic sense and includes treating agents, prophylactic agents, and replacement agents.

In one embodiment, the retroviral plasmid vector may be derived from Moloney Murine Leukemia Virus and is of the LN series of vectors, such as those hereinabove mentioned, and described further in Bender, et al., *J. Virol.*, Vol. 61, pgs. 1639–1649 (1987) and Miller, et al., *Biotechniques*, Vol. 7, pgs. 980–990 (1989). Such vectors have a portion of the packaging signal derived from a mouse sarcoma virus, and a mutated gag initiation codon. The term "mutated" as used herein means that the gag initiation codon has been deleted or altered such that the gag protein or fragments or truncations thereof, are not expressed.

In another preferred embodiment, the retroviral plasmid vector is derived from Moloney Murine Leukemia Virus and includes at least four cloning, or restriction enzyme recognition sites, wherein at least two of the sites have an average frequency of appearance in eukaryotic genes of less than once in 10,000 base pairs; i.e., the restriction product has an average DNA size of at least 10,000 base pairs. Preferred cloning sites are selected from the group consisting of NotI, SnaBI, SalI, and XhoI. In a most preferred embodiment, the retroviral plasmid vector includes each of these cloning sites. Such vectors are further described in U.S. patent application Ser. No. 08/340,805, filed Nov. 17, 1994, now U.S. Pat. 5,672,510, and in PCT Application No. W091/10728, published Jul. 25, 1991, and incorporated herein by reference in their entireties.

When a retroviral plasmid vector including such cloning sites is employed, there may also be provided a shuttle cloning vector which includes at least two cloning sites which are compatible with at least two cloning sites selected from the group consisting of NotI, SnaBI, SalI, and XhoI located on the retroviral plasmid vector. The shuttle cloning vector also includes at least one desired polynucleotide encoding a therapeutic agent which is capable of being transferred from the shuttle cloning vector to the retroviral plasmid vector.

The shuttle cloning vector may be constructed from a basic "backbone" vector or fragment to which are ligated one or more linkers which include cloning or restriction enzyme recognition sites. Included in the cloning sites are the compatible, or complementary cloning sites hereinabove described. Genes and/or promoters having ends corresponding to the restriction sites of the shuttle vector may be ligated into the shuttle vector through techniques known in the art.

The shuttle cloning vector can be employed to amplify polynucleotide sequences in prokaryotic systems. The shuttle cloning vector may be prepared from plasmids generally used in prokaryotic systems and in particular in bacteria. Thus, for example, the shuttle cloning vector may be derived from plasmids such as pBR322; pUC 18; etc.

The retroviral plasmid vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, TK promoters, and B19 parvovirus promoters. The selection of a suitable promoter will be apparent to those skilled in the art from the teachings contained herein.

Other retroviral plasmid vectors which may be employed include, but are not limited to, retroviral plasmid vectors derived from Human Immunodeficiency Virus, Rous Sarcoma Virus, avian leukosis virus, NZB virus, the feline endogenous virus RD114, feline leukemia virus B (FeLV-B), simian sarcoma associated virus (SSAV), baboon endogenous virus (BaEV), and gibbon ape leukemia virus (GALV). It is to be understood, however, that the scope of the present invention is not to be limited to any particular retroviral plasmid vector.

Polynucleotides encoding therapeutic agents which may be contained in the retroviral plasmid vector include, but are not limited to, polynucleotides encoding tumor necrosis factor (TNF) genes, such as TNF-α; genes encoding interferons such as Interferon-α, Interferon-β, and Interferon-γ; genes encoding interleukins such as IL-1, IL-1β, and Interleukins 2 through 14; genes encoding GM-CSF; genes encoding adenosine deaminase, or ADA; genes which encode cellular growth factors, such as lymphokines, which are growth factors for lymphocytes; genes encoding epidermal growth factor (EGF), and keratinocyte growth factor (KGF); genes encoding soluble CD4; Factor VIII; Factor IX; cytochrome b; glucocerebrosidase; T-cell receptors; the LDL receptor, ApoE, ApoC, ApoAI and other genes involved in cholesterol transport and metabolism; the alpha-1 antitrypsin (α1AT) gene; the insulin gene; the hypoxanthine phosphoribosyl transferase gene; the CFTR gene; negative selective markers or "suicide" genes, such as viral thymidine kinase genes, such as the Herpes Simplex Virus thymidine kinase gene, the cytomegalovirus virus thymidine kinase gene, and the varicella-zoster virus thymidine kinase gene; Fc receptors for antigen-binding domains of antibodies, antisense sequences which inhibit viral replication, such as antisense sequences which inhibit replication of hepatitis B or hepatitis non-A non-B virus; antisense c-myb oligonucleotides; and antioxidants such as, but not limited to, manganese superoxide dismutase (Mn-SOD), catalase, copper-zinc-superoxide dismutase (CuZn-SOD), extracellular superoxide dismutase (EC-SOD), and glutathione reductase; tissue plasminogen activator (tPA); urinary plasminogen activator (urokinase); hirudin; the phenylalanine hydroxylase gene; nitric oxide synthesase; vasoactive peptides; angiogenic peptides; the dopamine gene; the dystrophin gene; the β-globin gene; the α-globin gene; the HbA gene; protooncogenes such as the ras, src, and bcl genes; tumor-suppressor genes such as p53 and Rb; the LDL receptor; the heregulin-α protein gene, for treating breast, ovarian, gastric and endometrial cancers; monoclonal antibodies specific to epitopes contained within the β-chain of a T-cell antigen receptor; the multidrug resistance (MDR) gene; polynucleotides encoding ribozymes; antisense polynucleotides; genes encoding secretory peptides which act as competitive inhibitors of angiotensin converting enzyme, of vascular smooth muscle calcium channels, or of adrenergic receptors, and polynucleotides encoding enzymes which break down amyloid plaques within the central nervous system. It is to be understood, however, that the scope of the present invention is not to be limited to any particular therapeutic agent.

The polynucleotide encoding the therapeutic agent is under the control of a suitable promoter. Suitable promoters which may be employed include, but are not limited to, the retroviral LTR; the SV40 promoter; the cytomegalovirus (CMV) promoter; the Rous Sarcoma Virus (RSV) promoter; the histone promoter; the polIII promoter, the β-actin promoter; inducible promoters, such as the MMTV promoter, the metallothionein promoter; heat shock promoters; adenovirus promoters; the albumin promoter; the ApoAI promoter; B19 parvovirus promoters; human globin promoters; viral thymidine kinase promoters, such as the Herpes Simplex thymidine kinase promoter; retroviral LTRs; human growth hormone promoters, and the MxIFN inducible promoter. The promoter also may be the native promoter which controls the polynucleotide encoding the therapeutic agent. It is to be understood, however, that the scope of the present invention is not to be limited to specific foreign genes or promoters.

In another embodiment, the retroviral vector is produced by introducing a wild-type retrovirus into a cell line which is resistant to lysis by human serum, and recovering the resistant retroviral vector from the cell line. In one embodiment, the retrovirus is selected from the group consisting of Rous Sarcoma Virus, RD114, BaEV, SSAV, FeLV-B, GALV, avian leukosis virus, and murine leukemia viruses, such as, for example, Moloney Murine Leukemia Virus or amphotropic murine leukemia viruses (MLV-A), including, but not limited to, strains 4070A and 1504.

Preferably, the cell line is selected from the group consisting of HOS, TE671, HT1080, Mv-1-Lu, human 293 cells, or cell lines derived therefrom.

In one preferred embodiment, the retrovirus is MLV-A, and the cell line is the HOS cell line.

Applicants have found that when retroviral vectors are produced by introducing the above-mentioned retroviruses into the above-mentioned cell lines, the resulting retroviral vectors produced by the above-mentioned retrovirus/cell line combinations are resistant to inactivation by human complement proteins which are found in human serum.

Alternatively, a retroviral vector may be produced by introducing into a pre-packaging cell (i.e., a cell including polynucleotides encoding gag and pol proteins), which is resistant to lysis by human serum, a plasmid vector including a polynucleotide which encodes an envelope protein, such as a retroviral env protein, and a retroviral plasmid vector including a 5' LTR and a 3' LTR, a packaging signal, and at least one polynucleotide encoding a protein or polypeptide of interest. The gag and pol retroviral proteins may be obtained from any retrovirus, including, but not limited to, Moloney Murine Leukemia Virus, Rous Sarcoma Virus, the feline endogenous virus RD114, BaEV, gibbon ape leukemia virus (GALV), simian sarcoma associated virus SSAV, FeLV-B, human immunodeficiency virus, NZB virus, and avian leukosis virus. Alternatively, the gag/pol proteins may be modified or chimeric gag/pol constructs. The envelope may be obtained from any retrovirus, including, but not limited to, Moloney Murine Leukemia Virus, amphotropic murine leukemia viruses (MLV-A), Rous Sarcoma Virus, the feline endogenous virus RD114, BaEV, gibbon ape leukemia virus (GALV), SSAV, FeLV-B, human immunodeficiency virus, NZB virus, and avian leukosis virus. The envelope also may be an envelope which includes amphotropic and ecotropic portions. Alternatively, the env proteins may be modified or chimeric env constructs or obtained from non-retroviruses, such as vesicular stomatitis virus and HVJ virus.

Thus, in accordance with another aspect of the present invention, there is provided a retroviral vector resistant to inactivation by human serum which has been produced by introducing into a pre-packaging cell line, which is resistant to lysis by human serum, a plasmid vector including a polynucleotide encoding an envelope protein which may be obtained from a retrovirus including those selected from the group consisting of Moloney Murine Leukemia Virus, Rous Sarcoma Virus, the feline endogenous virus RD114, BaEV, SSAV, FeLV-B, gibbon ape leukemia virus (GALV), amphotropic murine leukemia viruses (MLV-A), human immunodeficiency virus, NZB virus, avian leukosis virus; or an envelope which includes amphotropic and ecotropic portions; or may be obtained from a non-retrovirus, such as vesicular stomatitis virus or HVJ virus; or which may be a modified or chimeric env construct; and a retroviral plasmid vector including a 5' LTR, a 3' LTR, a packaging signal, and at least one polynucleotide encoding a protein or polypeptide of interest. In accordance with yet another aspect of the present invention, there is provided a packaging cell line for generating retroviral vectors resistant to inactivation by human serum which includes a polynucleotide encoding an envelope protein as hereinabove described. Preferably, the packaging cell line includes a first plasmid vector including a polynucleotide encoding the gag and pol retroviral proteins, and a second plasmid vector encoding an envelope protein as hereinabove described. The packaging cell line is resistant to lysis by human serum.

In an alternative embodiment, the packaging cell can be constructed by introducing into a complement-resistant cell a single plasmid containing the desired gag, pol, and env genes.

As stated hereinabove, the polynucleotide encoding the gag and pol retroviral proteins may be obtained from any retrovirus, including, but not limited to, Moloney Murine Leukemia Virus, amphotropic murine leukemia viruses (MLV-A), Rous Sarcoma Virus, the feline endogenous virus RD114, BaEV, gibbon ape leukemia virus (GALV), SSAV, FeLV-B, NZB virus, and avian leukosis virus (ALV). Alternatively, the gag/pol proteins may be modified or chimeric gag/pol constructs. In general, the polynucleotide encoding the gag and pol retroviral proteins is contained in an appropriate plasmid vector. In one embodiment, the gag and pol retroviral proteins are obtained from Moloney Murine Leukemia Virus, and are contained in a plasmid known as pCRIPenv-, as described in Danos, et al., *Proc. Nat. Acad. Sci.*, Vol. 85, pgs. 6460–6464 (1988).

Another plasmid vector includes a polynucleotide encoding an envelope protein which may be obtained from any retrovirus, including, but not limited to, Moloney Murine Leukemia Virus, Rous Sarcoma Virus, the feline endogenous virus RD114, BaEV, SSAV, FeLV-B, gibbon ape leukemia virus (GALV), amphotropic murine leukemia viruses (MLV-A), human immunodeficiency virus, NZB virus, and avian leukosis virus, or non-retroviruses, such as vesicular stomatitis virus and HVJ virus, or modified or chimeric env constructs. In one alternative, the envelope protein includes amphotropic and ecotropic portions. The plasmid vectors encoding the gag and pol proteins, and the env protein and the retroviral plasmid vector hereinabove described, then are transfected into a cell which is resistant to lysis by human serum to provide a helper-free packaging cell line which will generate retroviral particles resistant to inactivation by human serum and which include gag and pol proteins such as, for example, those hereinabove described, an envelope protein which may be obtained from any retrovirus, including, but not limited to, Moloney Murine Leukemia Virus, Rous Sarcoma Virus, the feline endogenous virus RD114, BaEV, SSAV, FeLV-B, gibbon ape leukemia virus (GALV), amphotropic murine leukemia viruses (MLV-A), human immunodeficiency virus, NZB virus, avian leukosis virus, or non-retroviruses, such vesicular stomatitis virus and HVJ virus, or a modified or chimeric env construct, or an envelope including amphotropic and ecotropic portions. Such cell line may further include a retroviral plasmid vector including at least one polynucleotide encoding a protein or polypeptide of interest, such as a therapeutic agent, which may include those hereinabove described. Thus, the packaging cell line becomes a producer cell line which generates a retroviral vector which is resistant to inactivation by human serum which also includes at least one polynucleotide encoding a therapeutic agent. Such retroviral vector particles may be employed in gene therapy procedures such as those herein described, and may be administered to a human host in dosages such as those herein described.

In a preferred embodiment, the retroviral vector is produced in a cell line which is a human 293 cell line or a cell line derived from a human 293 cell line.

Applicants have discovered surprisingly that, when retroviral vectors are produced from a human 293 cell line or a cell line derived from a human 293 cell line, that such retroviral vectors are resistant to complement inactivation by human serum, and that such complement resistance is not dependent upon the envelope employed, even when the envelope is an amphotropic envelope.

The human 293 cell line and the cell lines derived from the human 293 cell line are resistant to lysis by human serum.

The term "human 293 cell line or a cell line derived from a human 293 cell line" as used herein, means the human 293 cell line (ATCC No. CRL 1573) (Graham, et al., *J. Gen. Virol.*, Vol. 36, pgs. 59–72 (1977)), or a cell line formed by transfecting 293 cells with one or more expression vehicles (e.g., plasmid vectors) including polynucleotides encoding various gag, pol, and env proteins. The envelope may be an amphotropic envelope, an ecotropic envelope, or a xenotropic envelope. Alternatively, the envelope may be obtained from vesicular stomatitis virus, or VSV, or other viruses described hereinbelow. Such cells also may include other polynucleotides such as, for example, polynucleotides encoding selectable markers. Examples of such cell lines include, but are not limited to, 293T/17 (ATCC No. CCRL 11268); Anjou 65 (ATCC No. CCRL 11269); Bosc 23 (CCRL 11270); and CAK8, also known as the Bing cell line (ATCC No. CCRL 11554). Such cell lines also are described in Pear, et al., *Proc. Nat. Acad. Sci.*, Vol. 90, pgs. 8392–8396 (September 1993), and in PCT Application No. WO94/19478, published Sep. 1, 1994.

Applicants have found unexpectedly that retroviruses, including retroviruses including an amphotropic envelope and murine leukemia virus based retroviruses, produced in the above-mentioned cell lines are resistant to inactivation (in particular, complement inactivation) or lysis by human serum. Thus, such retroviruses are suitable for in vivo administration to an animal host in gene therapy procedures.

The retroviral vectors, which are administered in vivo to an animal, can be produced by providing the human 293 cell line with the retroviral packaging function. Such packaging function may be provided by a replication competent retrovirus, or may be provided by a transient system which includes one or more expression vehicles (e.g., plasmid vectors) including polynucleotides encoding the gag, pol, and env proteins. Such functions also may be provided by stably transfecting the 293 cell line with one or more expression vehicles (e.g., plasmid vectors) including polynucleotides encoding the gag, pol, and env proteins. In addition to providing the 293 cells with the polynucleotides encoding the gag, pol, and env proteins, the 293 cells also are transfected with a retroviral plasmid vector as described hereinabove.

The retroviral plasmid vector is transfected into the packaging cell line which is a human 293 cell line or a cell line which is derived from a human 293 cell line, whereby such packaging cell line becomes a producer cell line that generates retroviral vectors which are resistant to inactivation by human serum. The packaging cell line derived from human 293 cells may be generated, for example, by immortalizing the cell line by transformation with transforming proteins such as the simian virus 40 (SV40) large tumor antigen; alternatively, one may use immortalized 293 cell lines such as 293T or 293E. Once the appropriate 293 cell line is chosen, it is necessary to co-transfect these cells with a plasmid encoding retroviral gag/pol proteins such as, for example, Moloney Murine Leukemia Virus gag/pol proteins, along with a plasmid containing a selectable marker such as hygromycin. Individual hygromycin resistance clones are isolated and screened both for the presence of the gag proteins (p15, p12, p30, and p10) and for reverse transcriptase (RT) activity. Routinely the clone expressing the highest levels of p30 and RT is designated the pre-packaging cell line. To generate a packaging cell line, it is necessary to co-transfect the pre-packaging cell line with an env-containing plasmid and a plasmid containing a selectable marker different than the one used in the first step (e.g., puromycin resistance, etc.). If the env component is toxic to the cell, such as is the case with many fusogenic envelopes, then it may be necessary to express this from an inducible promoter. Clones then are screened, and an appropriate packaging cell line is chosen. Such packaging cell lines also may be prepared as disclosed in Pear, et al., September 1993, or in PCT Application No. WO94/19478, published Sep. 1, 1994. In one embodiment, the packaging cell line is the CAK8 (or Bing) cell line (ATCC No. CCRL 11554), which is an amphotropic envelope-expressing packaging line, whereby the resultant retrovirus generated by such cell line has an amphotropic envelope. In another embodiment, the cell line is the Bosc 23 (ATCC No. CCRL 11270), which is an ecotropic envelope-expressing packaging line, whereby the resultant retrovirus generated by such cell line has an ecotropic envelope.

In yet another embodiment, the packaging cell line includes a polynucleotide encoding a vesicular stomatitis virus-G, or VSV-G envelope protein, whereby the resultant retrovirus includes such envelope. Such envelope protein is described further in Burns, et al., *Proc. Nat. Acad. Sci.,* Vol. 90, pgs. 8033–8037 (1993).

Other polynucleotides which encode viral envelopes, which may be contained in the packaging cell line, include, but are not limited to, polynucleotides encoding the envelope of Moloney Murine Leukemia Virus (MMLV); Rous Sarcoma Virus; the feline endogenous virus RD114; gibbon ape leukemia virus (GALV) envelope; baboon endogenous virus (BaEV) envelope; simian sarcoma associated virus (SSAV) envelope; amphotropic murine leukemia virus (MLV-A) envelope; human immunodeficiency virus envelope; avian leukosis virus envelope; the endogenous xenotropic NZB viral envelopes; and envelopes of the paramyxoviridiae family such as, but not limited to the HVJ virus envelope. (Morishita, et al., *Proc. Nat. Acad. Sci.,* Vol. 90, pgs. 8474–8478 (1993)). The polynucleotide also may encode a modified or chimeric envelope.

Thus, in accordance with another aspect of the present invention, there is provided a complement-resistant retroviral vector, which may be produced from a cell line selected from the group consisting of the HOS, TE671, HT1080, Mv-1-Lu, and human 293 cell lines, or a cell line derived from the HOS, TE671, HT1080, Mv-1-Lu, and human 293 cell lines, which includes an envelope selected from the group consisting of VSV-G envelope protein; Moloney Murine Leukemia Virus envelope; Rous Sarcoma Virus envelope; feline endogenous virus RD114 envelope; gibbon ape leukemia virus envelope; baboon endogenous virus envelope; simian sarcoma associated virus envelope; amphotropic murine leukemia virus (MLV-A) envelope; human immunodeficiency virus envelope; avian leukosis virus envelope; NZB viral envelopes; and HVJ virus envelope.

In addition, the envelope of the retrovirus may be modified such that the retrovirus is "targeted;" i.e., the retroviral envelope includes a protein or polypeptide which binds to a receptor on a desired target cell. Such target cells include, but are not limited to, primary cells, including blood cells, which includes all forms of nucleated blood cells as well as progenitors and precursors thereof; liver cells; endothelial cells; lymphocytes; and tumor cells, including malignant and non-malignant tumor cells.

The retroviral vectors are administered to an animal in vivo in an amount effective to produce a therapeutic effect in the animal. The animal may be a mammal, including human and non-human primates. The retroviral vectors may be administered systemically, for example, intravenously or intraarterially or intraperitoneally. The vectors also may be administered subcutaneously or intramuscularly. The retroviral vectors, which are resistant to inactivation by human serum, transduce cells in vivo, whereby the transduced cells express the therapeutic agent in vivo.

The retroviral vectors are administered to an animal in an amount effective to produce a therapeutic effect in the animal. In general, the retroviral vectors are administered in an amount of at least $10^5$ cfu, and in general such amount does not exceed $10^{12}$ cfu. Preferably, the retroviral vectors are administered in an amount of from about $10^6$ cfu to about $10^{10}$ cfu. The exact dosage to be administered is dependent upon various factors, including the age, height, weight, and sex of the patient, the disorder being treated, and the severity thereof.

The retroviral vectors are administered to the patient in a pharmaceutically acceptable carrier, such as, for example, a physiological saline solution. Other pharmaceutical carriers include, but are not limited to, mineral oil, alum, and lipid vesicles such as liposomes. The selection of a suitable pharmaceutical carrier is deemed to be within the scope of those skilled in the art from the teachings contained herein.

In one embodiment, the eukaryotic cells which are transduced in vivo are primary human cells. The gene encoding a therapeutic agent can be any gene having clinical usefulness, for example, therapeutic or marker genes. Preferably, the primary human cells are blood cells. The term "blood cells" as used herein is meant to include all forms of nucleated blood cells as well as progenitors and precursors thereof.

The gene carried by the blood cells can be any gene which directly enhances the therapeutic effects of the blood cells. The gene carried by the blood cells can be any gene which allows the blood cells to exert a therapeutic effect that it would not ordinarily have, such as a gene encoding a clotting factor (e.g., Factor VIII or Factor IX) useful in the treatment of hemophilia. The gene can encode one or more products having therapeutic effects. Examples of suitable genes include those that encode cytokines such as TNF, interleukins (interleukins 1–12), interferons (α, β, γ-interferons), T-cell receptor proteins and Fc receptors for binding to antibodies.

The retroviral vectors are useful in the treatment of a variety of diseases including but not limited to adenosine deaminase deficiency, sickle cell anemia, thalassemia, hemophilia, diabetes, α-antitrypsin deficiency, brain disorders such as Alzheimer's disease, and other illnesses such as growth disorders and heart diseases, for example, those caused by alterations in the way cholesterol is metabolized and defects of the immune system.

In one embodiment, the retroviral vectors may include a negative selectable marker, such as, for example, a viral thymidine kinase gene, and more particularly, the Herpes Simplex Virus thymidine kinase (TK) gene. Such retroviral vectors may be administered to tumor cells (in particular to cancer cells) in a human patient in vivo. The retroviral vectors then transduce the tumor cells. After the retroviral vectors have transduced the tumor cells, the patient is given an interaction agent, such as gancyclovir or acyclovir, which interacts with the protein expressed by the negative selectable marker in order to kill all replicating cells (i.e., the tumor cells) which were transduced with the retroviral vector including the negative selectable marker.

The retroviral vectors mentioned hereinabove also may be administered in an animal model for determining the effectiveness of a gene therapy treatment. For example, a retroviral vector, produced in a cell line which is resistant to lysis by human serum, and including a polynucleotide encoding a therapeutic agent, may be administered to animals of the same species in varying amounts. From determining the effectiveness of the gene therapy treatment in the animal, one may determine an effective amount of the retroviral vector to be administered to a human patient.

In another embodiment, the cells which are resistant to lysis by human serum, which have been transfected with a retroviral plasmid vector such as hereinabove described, which includes one or more polynucleotides encoding a therapeutic agent, whereby such cells have become producer cells, are administered to a patient in vivo, whereby the producer cells generate in vivo retroviral vector particles including a polynucleotide encoding a therapeutic agent.

Such an embodiment is applicable particularly to the treatment of tumors (including malignant and non-malignant tumors) such as, for example, brain tumors and head and neck tumors. For example, the producer cells may include a retroviral plasmid vector including a negative selectable marker. The producer cells then are administered to the tumor, whereby the producer cells generate retroviral vector particles including the polynucleotide encoding the negative selectable marker. The retroviral vector particles generated by the producer cells transduce the tumor cells, whereby the tumor cells produce the negative selectable marker. Upon administration of an interaction agent to the patient, the transduced tumor cells are killed.

Alternatively, the retroviral vector may transduce eukaryotic cells, in vitro, whereby the eukaryotic cells are cultured in vitro for the in vitro production of the therapeutic agent, or, alternatively, the transduced eukaryotic cells may be administered to a host as part of a gene therapy procedure, whereby the transduced eukaryotic cells express the therapeutic agent in vivo in a host.

In accordance with another aspect of the present invention, there is provided a method of identifying retroviral vectors that are resistant to inactivation by human serum comprising introducing a retrovirus into a cell line in which a resultant retroviral vector is to be produced. The resistance of the resultant retroviral vector to inactivation by human serum then is determined. The determination of the resistance of the resultant retroviral vector to inactivation by human serum may be made by methods described hereinbelow in the examples.

In accordance with another aspect of the present invention, there is provided a method of producing retroviral vectors resistant to inactivation by human serum. The method comprises determining resistance of cells to lysis by human serum. Resistance of cells to lysis by human serum may be determined by methods such as those described hereinbelow. Retroviral vectors then are produced from those cells found to be resistant to lysis by human serum.

EXAMPLES

The invention will now be described with respect to the following examples; however, the scope of the present invention is not intended to be limited thereby.

Example 1

Murine NIH 3T3 cells (ATCC No. CRL1658) were cultivated in Dulbecco's Modified Eagle's Medium (DMEM) supplemented with 10% newborn calf serum. Mink MV-1-Lu cells (ATCC No. CCL6584) were cultivated in DMEM with 10% fetal calf serum.

The MFGnlslacZ genome (Ferry, et al., *Proc. Nat. Acad. Sci.*, Vol. 88, pgs. 8377–8381 (1991) was introduced into NIH 3T3 and Mv-1-Lu cells by infection with lac Z (contained in Murine Leukemia Virus-A) produced from the ψCRIP packaging line containing MFGnlslacZ genome, as described in Tailor, et al., *J. Virol.*, Vol. 67, pgs. 6737–6741 (1993). MFGnlslacZ is a Moloney Murine Leukemia Virus based retroviral vector including a 5' LTR, a 3' LTR, a packaging signal, and a lacZ gene. After cell cloning by limiting dilution, clones which gave high titers of lac Z pseudotype in a pilot rescue experiment were selected. Lac Z pseudotypes containing helper virus were produced by infection of these cell clones with replication competent MLV-A 1504 strain. (Rasheed, et al., *J.Virol.*, Vol. 19, pgs. 13–18 (1976); Sommerfelt, et al., *Virology*, Vol. 176, pgs. 58–69 (1990); Tailor, et al., 1993). Viruses were harvested in serum-free Opti-MEM (Gibco U.K.). On the day before harvest, cells were washed once with Opti-MEM and incubated in Opti-MEM at 37° C. for 1 hour. The medium then was replaced with fresh Opti-MEM and cells were incubated overnight. Culture supernatant was harvested, filtered through a 0.45 μm filter, aliquoted, and stored as virus stock at −70° C. until use. All virus stocks had original lac Z titers ranging from $2 \times 10^4$ to $4 \times 10^6$ on appropriate assay cells.

Human serum was collected from a normal patient, aliquoted, and frozen at −70° C. until use. A portion of this serum was heat-inactivated at 56° C. for 1 hour.

40 μl of virus stock was mixed with an equal volume of fresh human serum or heat-inactivated human serum in 20 mM HEPES buffer, pH 7, and incubated at 37° C. for up to 1 hour. After incubation, the virus-serum mixture was diluted serially from 1:13 to 1:1,300 with DMEM/10% FCS with 8 μg/ml Polybrene and plated on TE671 cells in 24 well plates. Assay cells were seeded at $5 \times 10^4$ cells/well in 24 well plates on the day before infection. After 4 hours of infection, virus was removed and cells were cultivated in growth medium. Two days after infection, the cells were stained with X-gal in situ and lac Z positive colonies were counted as described. (Tailor, et al., 1993). Relative titers (%) for fresh (F) and heat-inactivated (HI) serum treatment are shown in FIG. 1A. As shown, in FIG. 1A, lac Z (MLV-A) from NIH 3T3 cells is indicated as 3T3A, and lac Z (MLV-A) from Mv-1-Lu cells is indicated as Mink A.

As shown in FIG. 1A, the virus produced from murine NIH 3T3 cells was inactivated rapidly. Five minutes of exposure to human serum decreased the viral titer more than 3 logs. The virus produced from Mv-1-Lu cells also was inactivated. After 1 hour of exposure to human serum, the viral titer was decreased by 2 logs.

In another experiment, murine NIH 3T3 cells and mink Mv-1-Lu cells were cultured as hereinabove described.

The MFGnlslacZ genome was introduced into NIH 3T3 and Mv-1-Lu cells, and then clones which gave high titers of lacZ pseudotype were selected as hereinabove described.

Lac Z (RD114) containing helper virus then was obtained from a NIH 3T3 cell clone with MFGnlslacZ genome by transfection with full length proviral DNA (sc3c, provided by Dr. S. O'Brien and described further in Reeves, et al., *J. Virol.*, Vol. 52, pgs 164–171 (1984)). A cell clone which gave high titers of lac Z pseudotype was selected. Lac Z pseudotypes containing helper virus were produced by infection of an Mv-1-Lu cell clone containing MFGnlslacZ genome with a replication competent RD114 virus as described previously. (Tailor, et al., 1993). The viruses were harvested in Opti-MEM, filtered through a 0.45 µm filter, and frozen at –70° C. until use. All virus stocks had original lac Z titers ranging from $2 \times 1^4$ to $4 \times 10^6$ on appropriate assay cells.

Figure 1B:
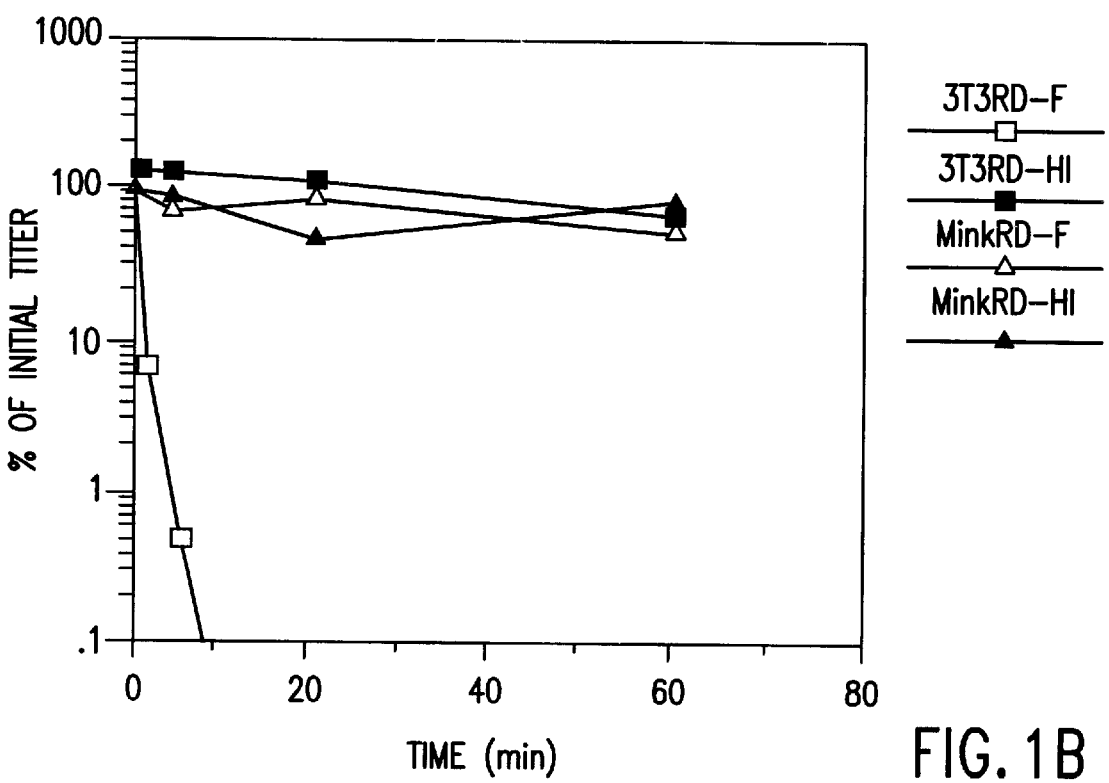

Virus stocks were mixed with equal volumes of fresh human serum or heat-inactivated human serum as hereinabove described, and incubated as hereinabove described. The virus-serum mixtures then were plated on TE671 cells as hereinabove described, virus then was removed, and the cells were cultivated in growth medium as mentioned hereinabove. The cells then were stained with X-gal in situ and lacZ positive colonies were counted as hereinabove described. Relative titers (%) for fresh (F) and heat-inactivated (HI) serum treatment are shown in FIG. 1B. As shown in FIG. 1B, lacZ (RD114) obtained from NIH3T3 cells is indicated as 3T3RD, and lacZ (RD114) obtained from mink Mv-1-Lu cells is indicated as Mink RD.

As shown in FIG. 1B, the titer of lacZ (RD114) produced from NIH3T3 cells was decreased by 2 logs within 5 minutes when exposed to normal human serum, whereas lacZ (RD114) produced by Mv-1-Lu cells was resistant to a 1 hour exposure to human serum. As shown in FIGS. 1A and 1B, the activity in human serum responsible for viral inactivation was heat labile. The results shown in FIGS. 1A and 1B show that viruses produced by Mv-1-Lu cells are more resistant to human serum than those produced by NIH3T3 cells.

Example 2

Sensitivity of Viruses Produced from Different Cell Lines to Human Serum

Murine NIH3T3 and PG13 (Miller, et al., *J. Virol.*, Vol. 65, pgs. 2220–2224 (1991) ATCC No. 10686), GP+EAM12 (Markowitz, et al., *Virology*, Vol. 167, pgs. 400–406 (1988)), and GP+E86 (Markowitz, et al., *J. Virol.*, Vol. 82, pgs. 1120–1124 (1988)) packaging cell lines were cultivated in Dulbecco's Modified Eagle's Medium (DMEM) supplemented with 10% newborn calf serum. Mink Mv-1-Lu, dog Cf 2ThS+L- (ATCC No. CRL1430), human HOS (ATCC No. CRL1543), and human TE671 cells (Sommerfelt, et al., 1990; Tailor, et al., 1993, ATCC No. CRL8805) were cultivated in DMEM supplemented with 10% fetal calf serum.

The MFGnlslacZ genome was introduced into NIH3T3, Mv-1-Lu, Cf2ThS+L-, HOS, and TE671 cells by infection with lacZ (contained in MLV-A) produced from the ψCRIP packaging line (Danos, et al., 1988) as described in Tailor, et al., 1993. After cell cloning by limiting dilution, clones which have high titer of lacZ pseudotype in a pilot rescue experiment were selected. LacZ pseudotypes containing helper virus were produced by infection of these cell clones with replication competent MLV-A 1504 strain, MLV-XNZB, RD114, BaEVM7, SSAV, GALV-SF, and FeLV-B as described in Tailor, et al., 1993. Viruses were harvested in either serum-free Opti-MEM or DMEM/10% fetal calf serum, filtered through a 0.45 µm filter, and frozen at –70° C. until use. LacZ (RD114) was obtained from NIH3T3 cells by transfection with full-length proviral DNA (sc3c, provided by Dr. S. O'Brien, and described further in Reeves, et al., *J. Virol.*, Vol. 52, pgs. 164–171 (1984)). Helper-free pseudotypes from NIH3T3 cells were obtained from PG13, GP+EAM12, and GP+E86 packaging lines either by transduction with helper-free lacZ (contained in MLV-A) or transfection of MFGnlslacZ. Helper-free pseudotypes from Mv1-Lu cells were obtained by transfection of Mv-1-Lu cells containing MFGnlslacZ with separate expression plasmids encoding MLV gag/pol genes and MLV-E, MLV-A, or RD114 envelope genes. All virus stocks had original lacZ titers ranging from $2 \times 10^4$ to $4 \times 10^6$ on appropriate assay cells.

Human serum then was collected from a normal individual, aliquoted, and frozen at –70° C. until use. Some of the serum was heat-inactivated at 56° C. for 1 hour.

Figure 2A:
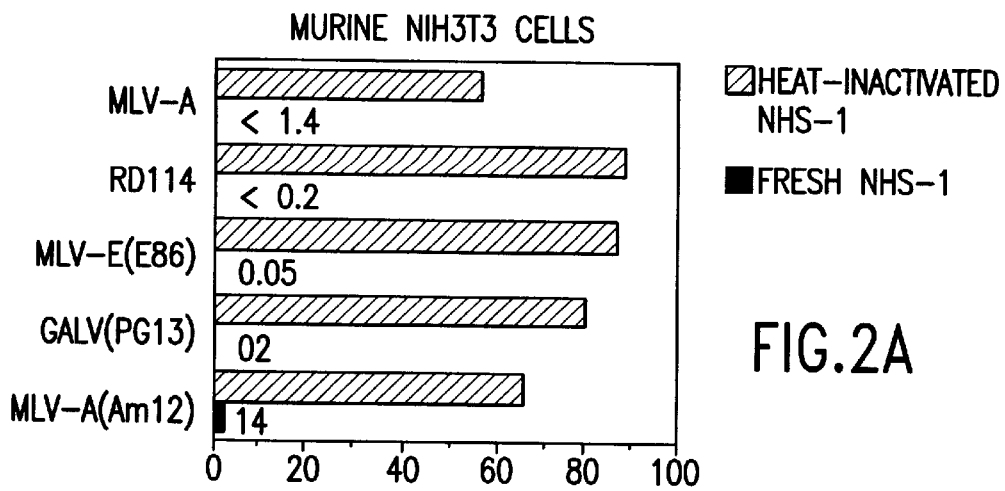
FIGS. 2A, 2B, 2C, 2D and 2E are graphs depicting the sensitivity of different viruses produced from different cell lines to human serum.
Figure 2C:
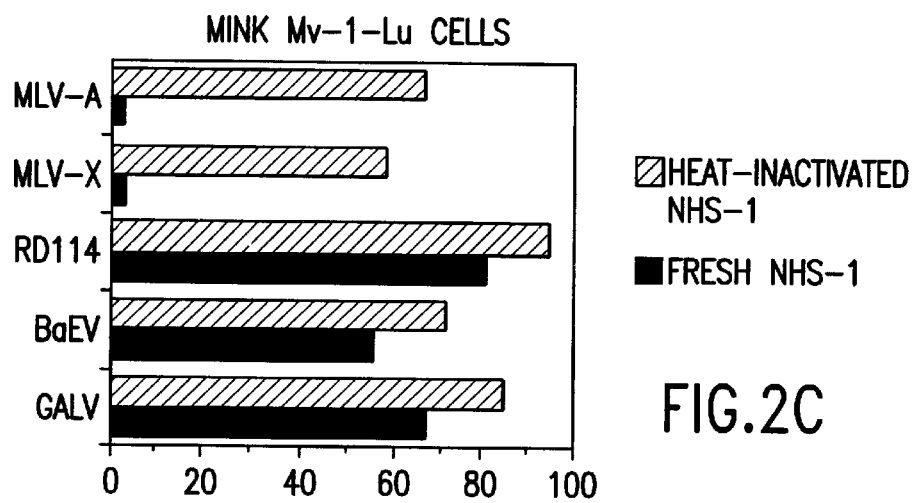
Figure 2E:
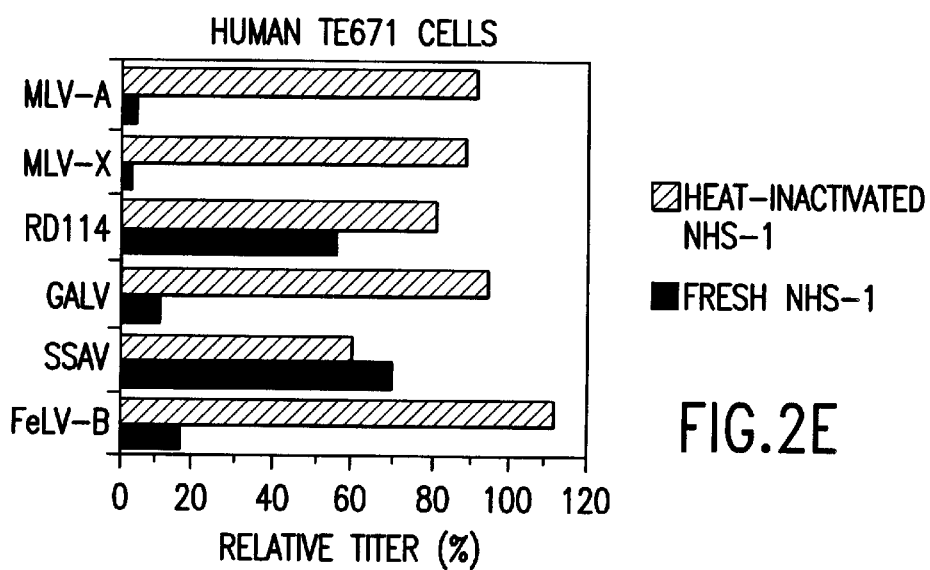
Figure 2B:
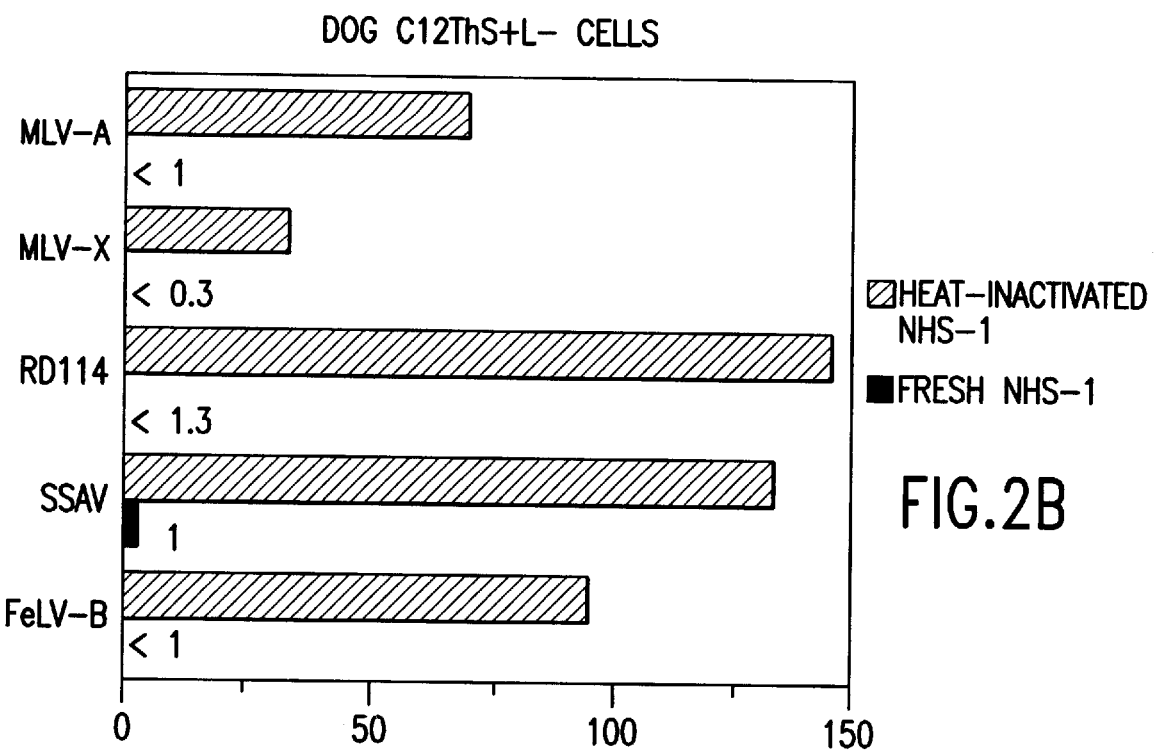
Figure 2D:
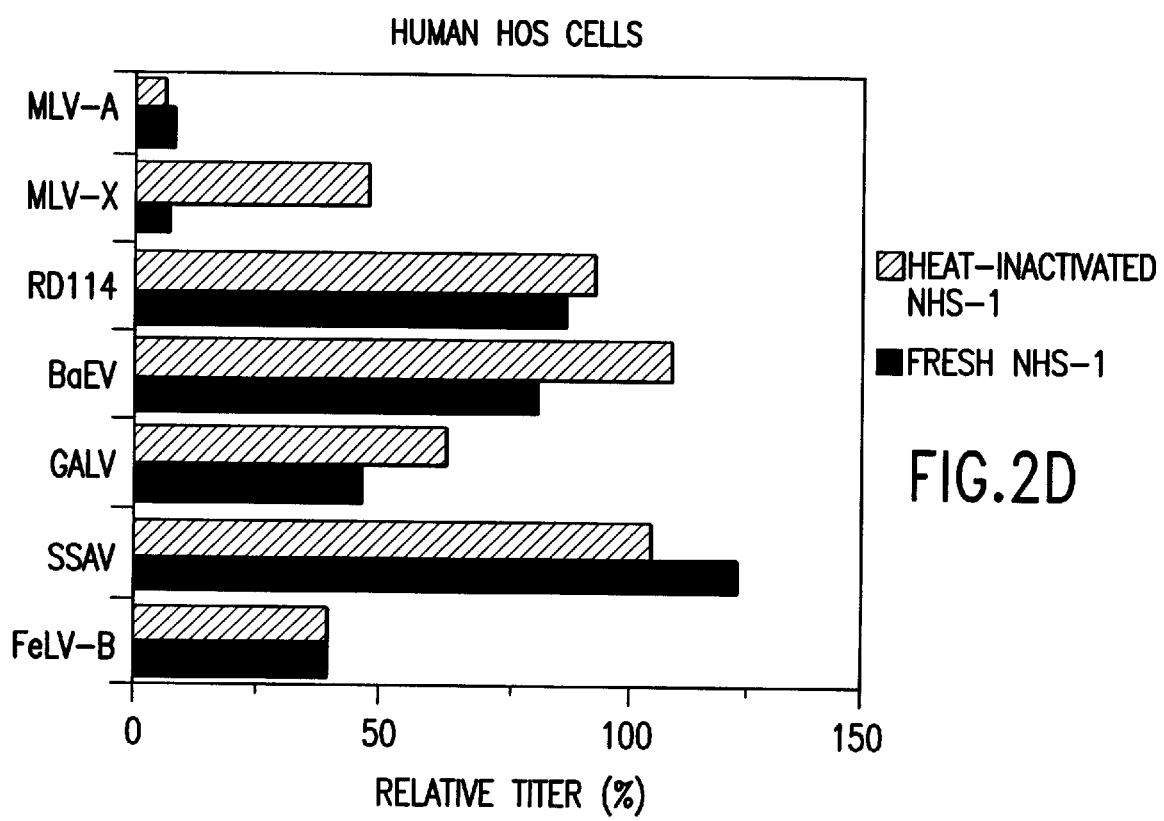

40 µl of virus dilution was mixed with an equal volume of fresh human serum, or heat-inactivated human serum in 20 mM HEPES buffer pH 7, with less than 2% fetal calf serum from virus harvest and incubated at 37° C. for up to 1 hour. After incubation, virus-serum mixture was diluted with 1 ml DMEM with 8 µg/ml Polybrene and plated on the assay cells in 24 well plates. MLV-E was assayed on NIH 3T3 cells; MLV-A, MLV-X (Levy, *Science*, Vol. 182, pgs. 1151–1153 (1973)), BaEV (Benveniste, et al., *Nature*, Vol. 248, pgs. 17–20 (1974)), and RD114 (McAllister, et al., *Nature New Biol.*, Vol. 235, pgs. 3–6 (1972)) were assayed on Mv-1-Lu or TE671 cells, and GALV (Kawakami, et al., *Nature New Biol.*, Vol. 235, pgs. 170–171 (1972)), SSAV (Thielen, etal., *J. Natl. Cancer Inst.*, Vol 47, pgs. 881–889 (1971)), and FeLV-B (Jarrett, et al., *J. Gen. Virol.*, Vol. 20, pgs. 169–175 (1973)) were assayed on TE671 cells. Assay cells were seeded at $5 \times 10^4$ cells/well in 24 well plates on the day before infection. After 4 hours of infection, virus was removed and cells were cultivated in growth medium. Two days after infection, the cells were stained with X-gal in situ and lacZ positive colonies were counted as described in Tailor, et al., 1993. Relative titers (%) for fresh and heat-inactivated human serum treatment versus fetal calf serum (FCS) treatment are shown in FIGS. 2A, 2B, 2C, 2D, and 2E. FIG. 2A shows virus titers for viruses generated from murine NIH3T3 cells, PG13 cells, GP+E86 cells, or GP+Am12 cells. FIG. 2B shows virus titers for viruses generated from dog Cf2ThS+L- cells; FIG. 2C shows virus titers for viruses generated from mink Mv-1-Lu cells; FIG. 2D shows virus titers for viruses generated from human HOS cells, and FIG. 2E shows virus titers for viruses generated from human TE671 cells.

As shown in FIG. 2A, retroviruses produced from NIH3T3 cells, as well as from GP+E86, PG13, and GP+Am12 cells were sensitive to inactivation by fresh human serum. In addition, viruses produced by the dog cell line Cf2ThS+L- all were sensitive to inactivation by human serum (FIG. 2B). As shown in FIG. 2C, however, while two murine leukemia viruses (MLV-A and MLV-X) produced by Mv-1-Lu cells were sensitive to human serum, the RD114, BaEV, and GALV viruses were resistant to inactivation by human serum. MLV-X was found to be sensitive to inactivation by human serum when produced by HOS or TE671 cells (FIGS. 2D and 2E). MLV-A was found to be resistant to complement inactivation when produced by HOS cells. RD114 and BaEV were found to be resistant when produced by these cell lines. GALV and FeLV-B were partially resistant when produced by these cell lines, and SSAV, which is closely related to GALV (Delassus, et al., Virology, Vol. 173, pgs. 205:213 (1989)), was resistant.

In order to determine which RD114 viral gene product(s) conferred resistance to human serum, recombinant virions were produced from Mv-1-Lu cells by expressing MLV gag and pol genes in combination with either MLV or RD114 env genes, as hereinabove described. The helper-free pseudotypes were obtained by transfection of MFGnlslacZ/Mv-1-Lu cells with separate expression plasmids encoding MLV gag and pol genes, and MLV-A, MLV-E, or RD114 env genes. The gag/pol plasmid was pCRIP env-, described in Danos, et al., 1988. Plasmids expressing the MLV-A, MLV-E, or RD114 env genes were derived from FB3 described in Heard, et al., *J. Virol.*, Vol. 65, pgs. 4026–4032 (1990) by inserting the MLV-A, MLV-E, or RD114 env genes downstream of the FB29 LTR promoter. The MLV-A virus, strain 4070A, indicated in Table I below, is described in Danos, et al., 1988. As shown in Table I below, virions with RD114 envelope were resistant to treatment with three fresh human serum samples for 1 hour, whereas those with amphotropic or ecotropic MLV envelopes were more sensitive. This demonstrates that envelope sequences can control sensitivity, in agreement with the assignment of p15E as the viral protein which triggers complement activation. (Bartholomew, et al., 1978.)

TABLE I

Inactivation of Recombinant Viruses Produced from Mv-1-Lu Cells

| | Relative Titer (%) | | |
|---|---|---|---|
| Virus | Serum Sample 1 | Serum Sample 2 | Serum Sample 3 |
| MLV-A (1502) | 2.7 | 5.5 | 10 |
| RD114 | 120 | 116 | 75 |
| MLV gag/pol+ MLV-A (4070A) env | 21 | 21 | 18 |
| MLV gag/pol+ RD114 env | 104 | 94 | 71 |
| MLV gag/pol+ MLV-E env | 32 | 23 | 26 |

Example 3

NIH3T3, Mv-1-Lu, Cf2ThS+L-, HOS, and TE671 cells containing MFGnlslacZ provirus, were infected with MLV-A, MLV-X, or RD114 virus, as described in Examples 1 and 2. $2 \times 10^6$ uninfected or infected cells then were removed from the plates with EDTA, washed, and resuspended in 200 μl of sodium [$^{51}$Cr] chromate (1 mCi/ml, Amersham) at 37° C. for 1 hour. After labeling, the cells were washed and resuspended in DMEM with 10% FCS. After incubation at 37° C. for 30 minutes, the cells were collected by centrifugation, washed with serum-free DMEM, and resuspended in serum-free DMEM at $2 \times 10^5$ cells/ml. 50 μl of cell suspension was mixed with 100 μl of serum dilution in a V-bottom microtiter well. Serum dilutions were 2/3, 2/9, 2/27, and 2/81. The plates were incubated at 37° C. for 1 hour and the percent-specific $^{51}$Cr released into cell-free supernatant was determined by the following formula:

(release with serum-release with serum-free medium)/(release with 1% NP40-release with serum-free medium)×100

NP40 is Nonidet P40 (Sigma).

Figure 3:
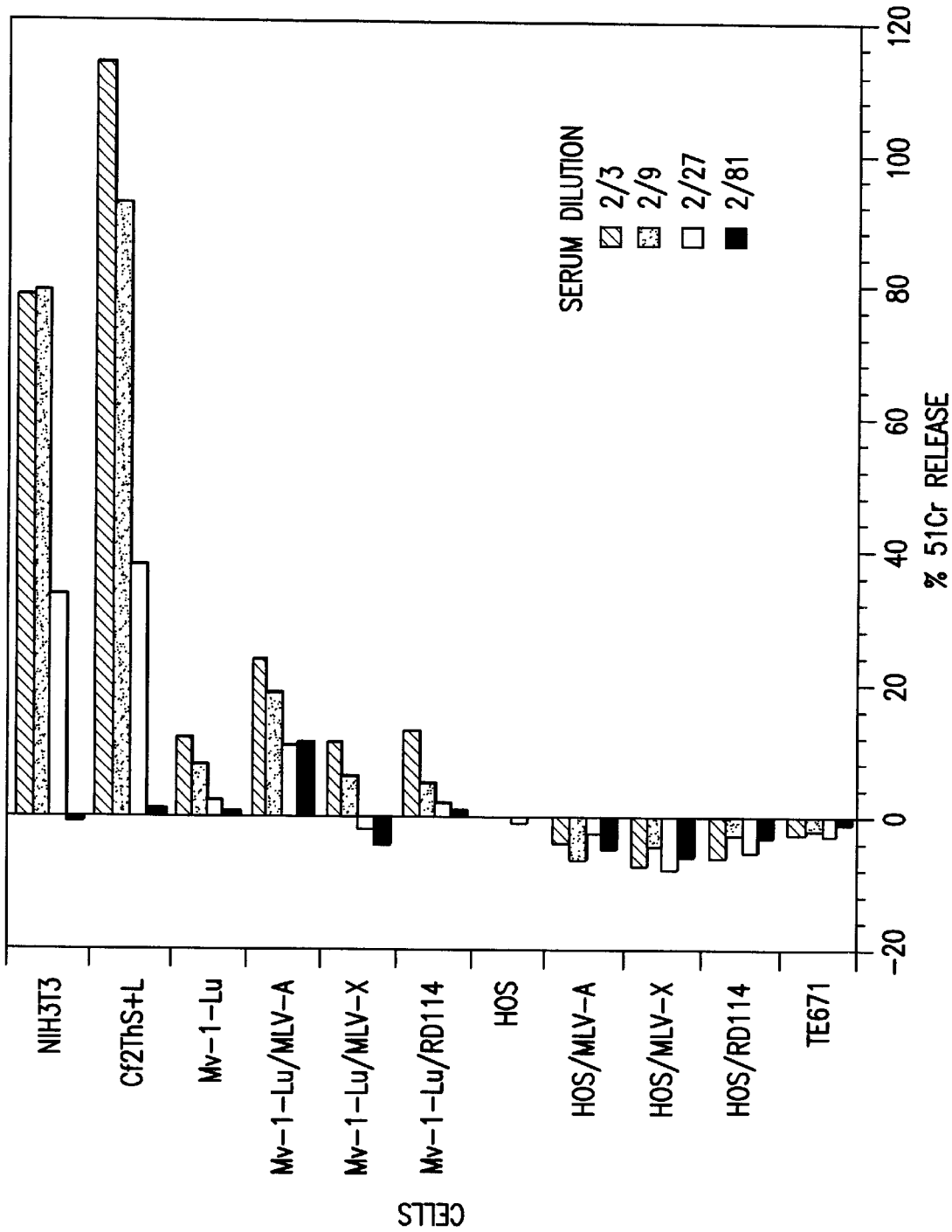
FIG. 3 is a graph depicting the cytotoxicity of fresh human serum to various producer cell lines.

The results of this assay are shown in FIG. 3. As shown in FIG. 3, NIH3T3 cells and Cf2ThS+L- cells were highly sensitive to lysis by human serum. Mv-1-Lu, HOS, and TE671 cells were resistant to lysis. Viral infection of the cells did not affect their sensitivity. Infection of Mv-1-Lu or HOS cells with MLV-A or MLV-X did not render them sensitive to lysis by human serum. These data suggest that a cellular factor(s), which can protect the uninfected cells from lysis by human serum, may be incorporated into virions produced from mink and human cells. Alternatively, a cellular factor(s), which enhances cell lysis by human serum may be incorporated into virions produced from mouse and dog cells. This latter possibility was supported by an observation that retroviruses made by mouse and dog cells were found to be inactivated by human serum mainly via recognition of sugar epitopes, Gal (α1–3) Gal epitopes, by natural antibodies. (Takeuchi, et al., unpublished data.) A viral effect, which does not affect the lysis of infected producer cells, also controls the differential sensitivity of viruses produced from a given cell.

Example 4

MLV-A, MLV-X, and RD114 viruses produced from mink Mv-1-Lu cells, HOS cells, or TE671 cells, as described in Examples 1 and 2, were treated with eight samples of normal human serum (also hereinafter referred to as NHS-1 through NHS-8) at 37° C. for 1 hour, and then the viruses were plated on TE671 cells. Relative titers (%) versus FCS treatment, of surviving lacZ psuedotypes are shown together with the mean value of relative titers in FIG. 4.

Figure 4:
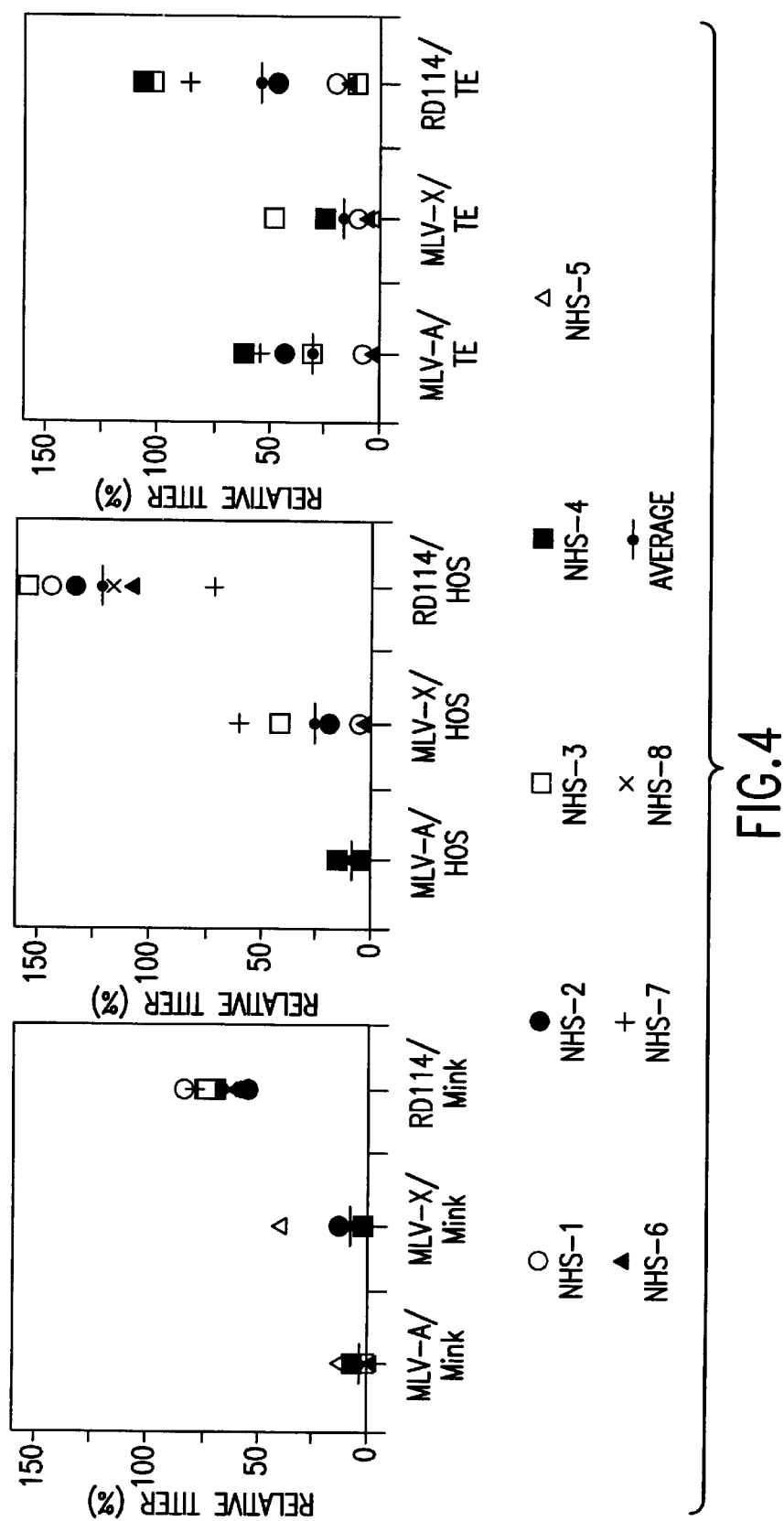
FIG. 4 shows graphs depicting the sensitivity of MLV-A, MLV-X, and RD114 viruses produced from mink Mv-1-Lu, HOS, and TE671 cell lines to eight different samples of human serum.

As shown in FIG. 4, RD114 produced from Mv-1-Lu or HOS cells was universally resistant. Results obtained with TE671 cells showed a more variable pattern of inactivation. The above results indicate that resistance to inactivation may not only be dependent upon the species of animal from which the producer cell line is obtained, but also may vary between cell lines from a particular species.

Example 5

MLV-A and RD114 viruses were produced from NIH3T3 cells or mink Mv-1-Lu cells as described in Examples 1 and 2. The viruses were harvested in serum-free Opti-MEM.

Serum samples NHS-1, NHS-3, and NHS-7 from Example 4 also were employed in this example, as well as serum samples from a C2 deficient patient, two C7 deficient patients, and a C9 deficient patient. All serum samples were aliquoted and frozen at −70° C. until use. In one experiment, sample NHS-7 was treated with cobra venom factor, another portion of NHS-7 was subjected to a 1:3 dilution, and a portion of NHS-7 was treated with C1. The cobra venom factor (CVF) treatment was done with solid phase CVF; i.e., the CVF was bound to Sepharose CL-4B. Serum samples were treated with 25 μg of cobra venom factor per ml of serum overnight at 37° C. Cobra venom factor is described further in Vogel, *Handbook of Natural Toxins,* Vol. 5, Reptile and Amphibian Venoms, Tu, ed., Marcell Dekker, New York, pg. 147 (1991). C1-treated NHS-7 was prepared by treating one part NHS-7 with 2 parts C1(titrated to give total C4 depletion) at 37° C. for 1 hour.

Viruses were tested for inactivation by human serum according to the procedures of Examples 1 and 2. The results are shown as relative titer (%) for serum samples treatment versus FCS treatment in Table 2 below. As shown in Table 2, C2D is the C2 deficient sample, C7D-1 and C7D-2 are the C7 deficient samples, and C9D is the C9 deficient sample.

TABLE 2

| Serum | Relative Titer (%) | | |
|---|---|---|---|
| | 3T3/MLV-A | 3T3/RD114 | Mv-1-Lu/MLV-A |
| CVF[a] treated | | | |
| NHS-7 | 130 ± 16[b] | 91 ± 1 | 112 ± 3 |
| NHS-7 | 0.97 ± 0.50 | 0.58 ± 0.08 | 28 ± 16 |
| C1 treated | | | |
| NHS-7 | 150 ± 13 | 107 ± 13 | 96 ± 16 |
| NHS-7 (1:3 dilution) | 11.7 ± 2.6 | 14.1 ± 0.8 | 37 ± 9 |
| C2D | 72[c] | 25 ± 8 | 147 ± 16 |
| C7D-1 | <1 | 0.15 | 2.5 |
| C7D-2 | 5.8 | 1.6 ± 0 | 7.8 ± 1.4 |
| C9D | <1 | <0.2 | 9.1 ± 3.9 | a - cobra venom factor
b - mean ± standard error of two experimental values
c - a single experiment was done In another experiment, MLV-A and RD-114 viruses generated from NIH3T3 or mink Mv-1-Lu cells were tested for lysis by serum samples NHS-3, NHS-7, and C7D-2 in a reverse transcriptase assay. In this assay, 12 ml of cell supernatant was harvested from confluent producer cells in serum-free Opti-MEM and clarified by low speed centrifugation and by filtration at 0.45 $\mu$m. The virus was concentrated by ultracentrifugation (12,000×g, 1 hour, 4° C.). The viral pellet then was suspended in 120 $\mu$l of cold Opti-MEM and aliquoted in 4 tubes (30 $\mu$l each). 30 $\mu$l of 0.5% Triton, FCS, and human serum were added, and the tubes were incubated at 1 hour at 37° C. Reverse transcriptase activity was measured as described in Goff, et al., *J. Virol.*, Vol. 38, pgs. 239–248 (1981). 80 $\mu$l of reverse transcriptase mix containing 5 $\mu$l of Tris (1M, pH 8.0), 5 $\mu$l dithiothreitol (0.1M), 2.5 $\mu$l MnCl$_2$ (0.04M), 10 $\mu$L KCl (1M), 1 $\mu$l primer-template (1 mg/ml of poly (rA), p(dT) 12–18, Pharmacia), 31.5 $\mu$l H$_2$O, and 20 $\mu$l $^3$H-TTP (0.1 mCi/ml of [Me-$^3$H]-thymidine triphosphate, Amersham), and 20 $\mu$l of virus/serum mixture were added to wells of a 96 well plate. Duplicate reactions were incubated at 37° C. Polymerized TTP was separated from free TTP on DE81 filter mats pre-wetted with 2×SSC using a cell harvester. Filters were washed for 30 seconds with 2×SSC, dried, and each spot was counted. Percent specific reverse transcriptase released by serum was estimated according to the formula:

(release by serum-release by FCS)/(release by Triton-release by FCS)×100

The results of this assay are shown in Table 3 below.

TABLE 3

| | Virus lysis RT release (% Triton X-100) | | | |
|---|---|---|---|---|
| Serum sample | 3T3/MLV-A | 3T3/RD114 | Mink/MLV-A | Mink/RD114 |
| NHS-7 | 39 ± 4 | 13 ± 5 | 21 ± 5 | 3 ± 1 |
| NHS-3 | 150 ± 1 | 61 ± 15 | 63 ± 2 | 16 ± 2 |
| C7D-2 | −0.7 ± 0.3 | 7 ± 8 | −6 ± 1 | −7 ± 2 |

The results shown in Table 2 indicate that depletion of complement from normal human serum, either by addition of cobra venom factor or complement component C1, resulted in the loss of its ability to inactivate MLV-A produced from NIH3T3 cells or Mv-1-Lu cells, and RD114 produced from NIH3T3 cells. Thus, as reported previously (Welsh, et al., 1975), the inactivation of MLV-A and RD114 by human sera was due to complement. C1 addition specifically depletes the classical pathway of complement activation. The above data, therefore, is in agreement with the previous report of involvement of the classical pathway of retroviral inactivation by human serum. (Cooper, et al., *J. Exp. Med.*, Vol. 144, pgs. 970–984 (1976)).

C2 deficient serum, which is unable to trigger the classical pathway of complement, also failed to inactivate MLV-A or RD114, as shown in Table 2. Sera deficient in two of the complement components common to both the classical and alternative pathways, C7 and C9, were still effective in viral inactivation (Table 2). C7 and C9 are involved in the final steps of complement-mediated lysis and are components of the membrane attack complex (MAC). The above data thus demonstrated that a step prior to C7 deposition was sufficient for inhibition of retroviral infectivity.

In addition, as reported previously (Welsh, et al., 1975), normal human serum was able to cause reverse transcriptase release from virions (Table 3). The results shown in Tables 2 and 3 also showed that MLV-A produced from Mv-1-Lu cells was more sensitive to lysis than RD114, and virus produced from NIH3T3 cells was more sensitive than virus produced from Mv-1-Lu cells. The C7 deficient serum which inhibited viral infectivity, however, failed to induce virion lysis. The above data demonstrate that some steps in activation of complement by the classical pathway, prior to the final stage of virion lysis, is sufficient for inhibition of retroviral infection by human serum.

Example 6

MFGnlslacZ genome and replication competent RD114 or MLV-A virus were introduced into HT 1080 cells by infection with helper positive lacZ pseudotypes produced by TE671 cells as described in Example 2. Five days after infection, virus was harvested in Opti-MEM as described in Example 1. Inactivation of virus with one of fresh (F) or heat-inactivated (HI) human serum samples NHS-1, NHS-2, or NHS-6 was assayed as described in Example 2. The results are shown in Table 4 below as relative titer for human serum treatment versus FCS treatment.

TABLE 4

| | Relative titer (%) | |
|---|---|---|
| Serum | RD114 | MLV-A |
| NHS-1 (F) | 129 | 26 |
| NHS-1 (HI) | 114 | 36 |
| NHS-2 (F) | 126 | 62 |
| NHS-2 (HI) | 96 | 113 |
| NHS-6 (F) | 140 | 13 |
| NHS-6 (HI) | 150 | 103 |

As shown in Table 4, the RD114 viruses produced by HT1080 cells were found to be resistant to inactivation by human serum, while the MLV-A viruses produced by HT1080 cells were found to be sensitive to fresh human serum.

Example 7

Construction of pG1Na

Figure 5:
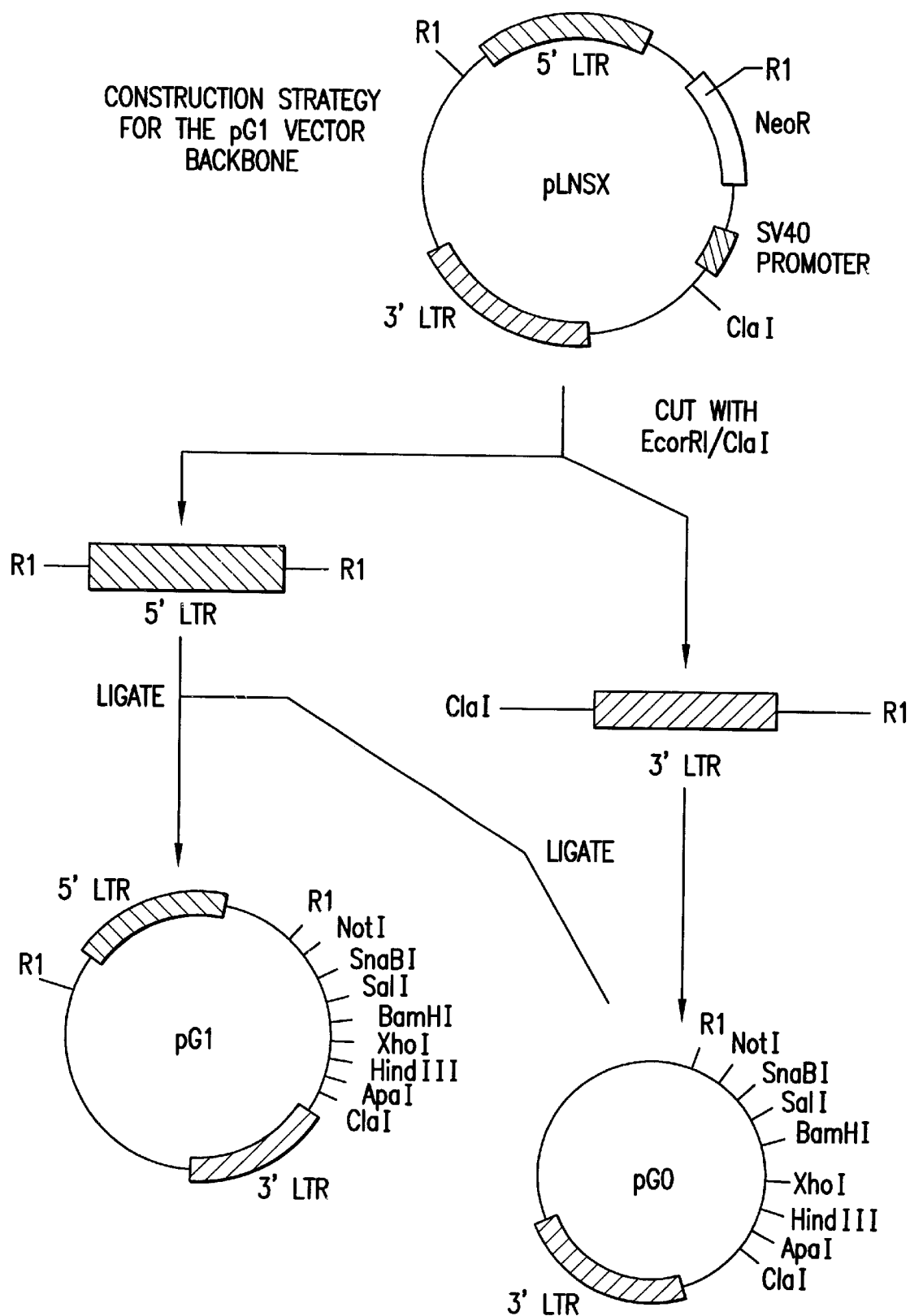
FIG. 5 is a schematic of the construction of plasmid pG1.
Figure 7:
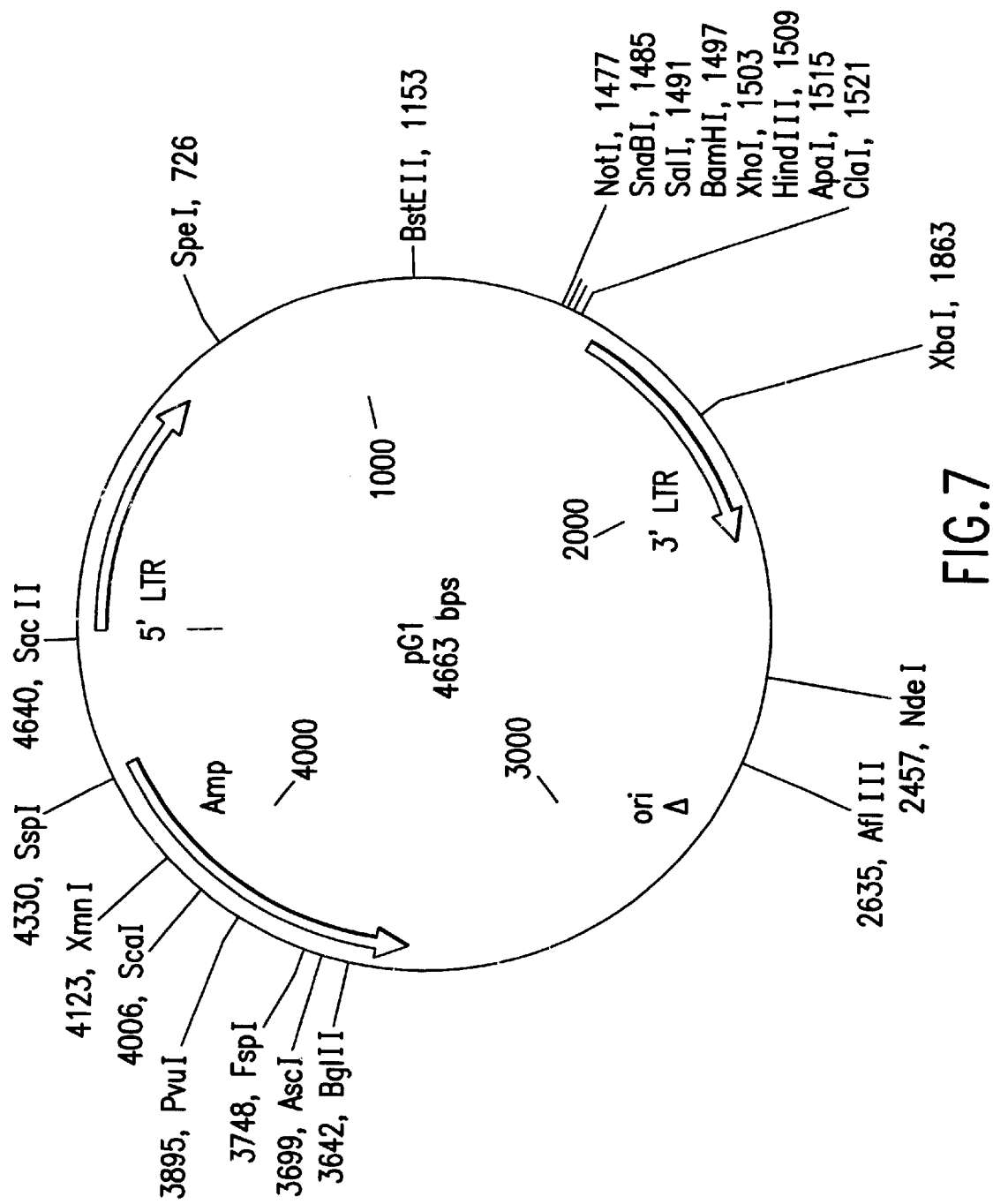
FIG. 7 is a map of plasmid pG1.

Plasmid pG1Na was derived from plasmid pG1. Plasmid pG1 was constructed from pLNSX (Palmer, et al., *Blood*, Vol. 73, pgs. 438–445). The construction strategy for plasmid pG1 is shown in FIG. 5. The 1.6 kb EcoRI fragment, containing the 5' Moloney Murine Sarcoma Virus (MoMuSV) LTR, and the 3.0 kb EcoRI/ClaI fragment, containing the 3' LTR, the bacterial origin of replication and the ampicillin resistance gene, were isolated separately. A linker containing seven unique cloning sites was then used to close the EcoRI/ClaI fragment on itself, thus generating the plasmid pGO. The plasmid pGO was used to generate the vector plasmid pG1 (FIG. 7) by the insertion of the 1.6 kB EcoRI fragment containing the 5' LTR into the unique EcoRI site of pGO. Thus, pG1 (FIG. 7) consists of a retroviral vector backbone composed of a 5' portion derived from MoMuSV, a short portion of gag in which the authentic ATG start codon has been mutated to TAG (Bender, et al. 1987), a 54 base pair multiple cloning site (MCS) containing, from 5' to 3', the sites EcoRI, NotI, SnaBI, SalI, BamHI, XhoI, HindIII, ApaI, and ClaI and a 3' portion of MoMuLV from base pairs 7764 to 7813 (numbered as described Van Beveren, et al., *Cold Spring Harbor*, Vol. 2, pg. 567, 1985) (FIG. 6). The MCS was designed to generate a maximum number of unique insertion sites, based on a screen of non-cutting restriction enzymes of the pG1 plasmid, the $neo^r$ gene, the β-galactosidase gene, the $hygromycin^r$ gene, and the SV40 promoter.

Figure 8:
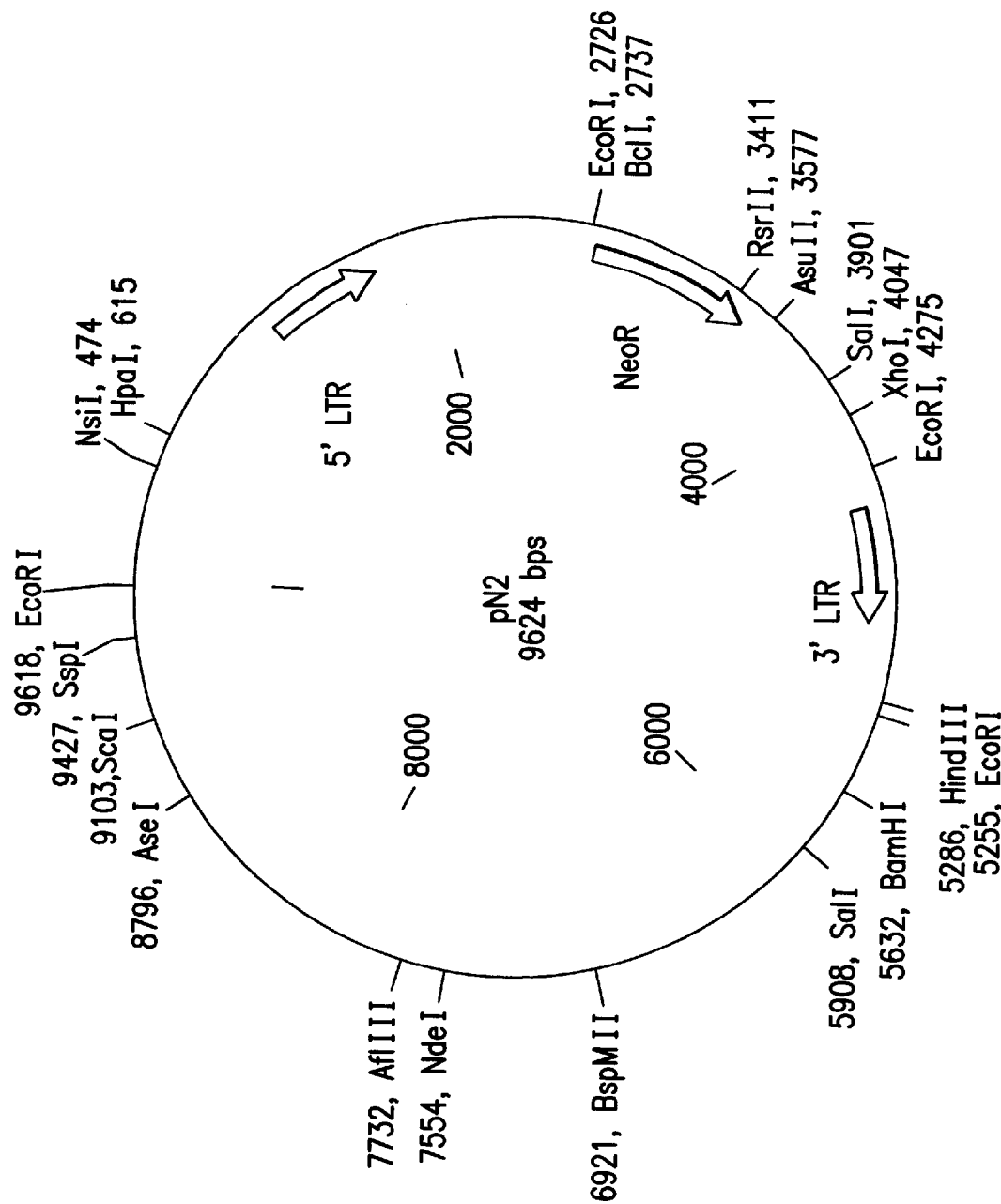
FIG. 8 is a map of plasmid pN2.
Figure 9:
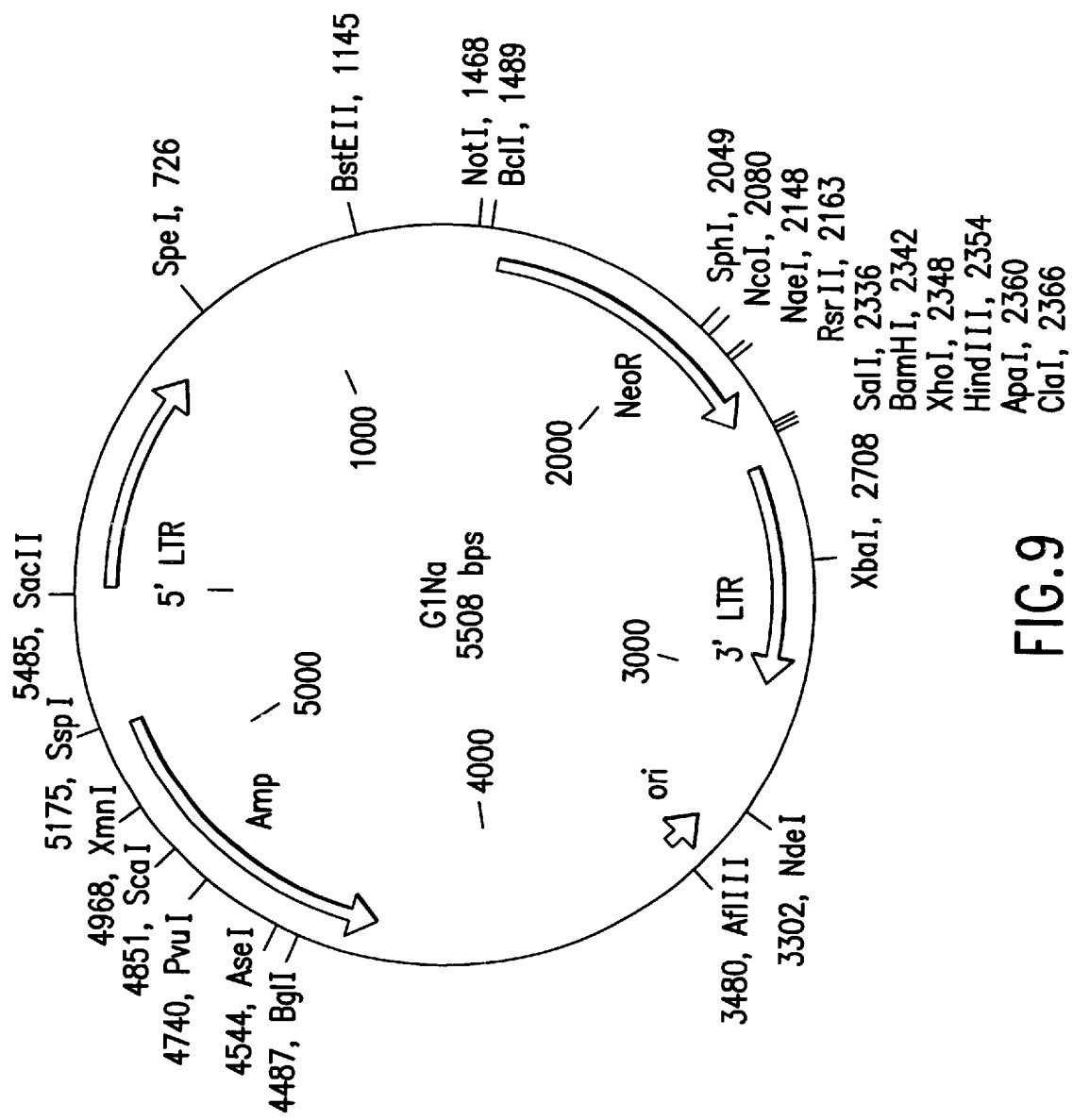
FIG. 9 is a map of plasmid pG1Na.

The vector pG1Na was constructed from pG1 and pN2 (Armentano, et al., *J. Virology*, Vol. 61, pgs. 1647–1650 (1987)). pG1Na was constructed by cutting pN2 (FIG. 8) with EcoRI and AsuII, filling in the ends of the EcoRI/AsuII fragment containing the $neo^R$ gene, and ligating the fragment into SnaBI digested pG1 to form pG1Na (FIG. 9).

Example 8

In order to determine the effect of human serum on cell viability, a flow cytometry based assay using propidium iodide (PI) was performed on HOS cells and NIH3T3TK- cells. Adherent cells were harvested by trypsinization, and initial viability assessed by Trypan Blue exclusion. Cells were incubated with fresh human serum or heat-inactivated human serum at 37° C. for 30 minutes, and then washed with PBS two times. Immediately prior to analysis on a Becton-Dickinson FACScan, PI (0.8 µg/ml final concentration) was added. Analysis of data was performed on FL2 (red) fluorescence, and percent live cells calculated from the best separation of PI stained (dead) and unstained (live) cells. The results are given in Table 5 below.

TABLE 5

| cells | human serum | % live | % dead |
| --- | --- | --- | --- |
| NIH3T3Tk- | inactivated | 96.4 | 3.6 |
| NIH3T3Tk- | normal | 22.5 | 77.5 |
| HOS | inactivated | 86.4 | 13.6 |
| HOS | normal | 89.2 | 10.8 |

The above results indicate that the HOS cells are resistant to human serum.

pG1Na was transfected into the ectotropic PE501 cell line ($5\times10^5$ cells) by calcium phosphate precipitation. After transfection, 10 ml of vector supernatant was added to a culture of $5\times10^5$ amphotropic PA317 cells. After addition of the vector supernatant to the PA317 cells, the cells were cultured in the presence of G418. A selected population of cells generates the amphotropic vector G1Na. Vector supernatant (5–10 ml) from the selected population of cells, and which contains G1Na was used to infect HOS cells and NIH3T3TK⁻ cells. 24 hours post infection, vector supernatant was removed and the cells selected in G418 until a stable population was generated. Selected HOS/G1Na or NIH3T3TK-/G1Na populations were plated in T-25 flasks at subconfluent densities. The following day, the cell monolayers were infected with 4070A, a replication competent amphotropic retrovirus in the presence of Polybrene. 8 hours post infection, the viral supernatant was removed and the cells refed with fresh medium. Once the cells reached confluence, they were split at a 1:10 dilution. This cycle was repeated an additional 2 times to ensure that all the cells had been infected with the wild-type virus. A 24 hour supernatant was collected once the cells had reached confluence. Viral supernatant which contains both wild-type 4070A and pseudotyped G1Na was spun for 10 minutes at 2,000 rpm (4° C.) followed by filtration through a 0.45 µm filter. The filtered supernatant was divided in small aliquots, flash frozen to dry, and transferred to −70° C. for long-term storage.

Ten microliters of filtered virus supernatant was mixed with ninety microliters of fresh human serum (HS), heat-inactivated human serum (ΔHS), or heat-inactivated FBS (ΔBS) at 37° C. for 45 minutes. After incubation, the virus-serum mixture was immediately added to 1 ml of DMEM containing Polybrene followed by serial 10-fold dilutions in the same medium. (Please provide number of dilutions.) One ml, in duplicate, of each dilution was immediately plated on a subconfluent monolayer of NIH3T3TK- cells for 12 hours at 37° C. The following day, viral medium was removed and replaced with fresh DMEM containing 0.8 mg/ml G418. Inactivation (fold decrease) was determined by dividing the titer obtained in the presence of heat-inactivated human serum by the titer obtained in the presence of human serum. The results are given in Table 6 below.

TABLE 6

| sample | titer @t = O | ΔFBS @ 45 min | ΔHS @ 45 min | HS @ 45 min | ΔHS/HS ratio |
| --- | --- | --- | --- | --- | --- |
| G1Na/ NIH 3T3Tk- + 4070A | $1.85 \times 10^6$ | $1.6 \times 10^6$ | $1.1 \times 10^6$ | $7.4 \times 10^3$ | 148-fold decrease |
| G1Na/ HOS + 4070A | $2.1 \times 10^5$ | $2.65 \times 10^5$ | $4.6 \times 10^4$ | $2.7 \times 10^4$ | 1.76-fold decrease |

The above results show that HOS cells are capable of producing amphotropic Murine Leukemia Virus based vectors that are resistant to lysis by human serum.

Example 9

This example compares the sensitivity of retroviral vectors including pG1Na containing either an amphotropic envelope produced from PA317 cells, an amphotropic envelope from human CAK8 cells, or a VSV-G envelope from a stable mouse cell line (gp7C).

The CAK8 cell line (ATCC No. CCRL 11554) was derived from the 293T cell line (Pear, et al., *Proc. Nat. Acad. Sci.*, Vol. 90, pgs. 8392–8396 (September 1993). The CAK8 cell line includes a polynucleotide encoding a retroviral envelope derived from the amphotropic 4070A retrovirus, wherein the polynucleotide sequence encoding the 35 C-terminal amino acids of 4070A retrovirus is replaced with a polynucleotide encoding the 35 C-terminal amino acids of an ecotropic virus. A clone, termed 293/17, was isolated from a 293T population (Du Bridge, et al., *Mol. Cell. Biol.*, Vol. 7, pgs. 379–387 (1987)) that produced retroviral supernatants capable of infecting NIH 3T3 cells at titers greater than $10^6$/ml following transient transfection with wild-type Moloney virus (pZap) (Shoemaker, et al., *J. Virol.,* Vol. 40, pgs. 164–172 (1981)), and a β-galactosidase-expressing retroviral vector pBND8 (Pear, et al., 1993). The gag-pol expressing plasmid, pCripEnv- (Danos, et al., *Proc. Nat. Acad. Sci.,* Vol. 85, pgs. 6460–6464 (1988)), which contains a mutation in the envelope region, lacks the packaging site, and replaces the 3' LTR with the SV40 poly (A) site, was transfected into 293T/17 cells along with a plasmid conferring hygromycin resistance. (Bernard, et al., *Exp. Cell. Res.,* Vol. 158, pgs. 237–243 (1985)). Individual clones were selected and tested for reverse transcriptase activity (Goff, et al., *J. Virol.,* Vol. 38, pgs. 239–248 (1981)), and one clone, Anjou 65, had the highest reverse transcriptase activity. The amphotropic envelope expressing construct, pCripAMgag- (Danos, et al., 1988), which contains mutations in the gag region, lacks the packaging site, and replaces the 3' LTR, was transfected into Anjou 65 cells along with a plasmid expressing the gpt resistance gene. (Jasin, et al., *Genes and Dev.,* Vol. 2, pgs. 1353–1363 (1988)). Individual clones were isolated and tested for the ability to produce high titer β-galactosidase-expressing retroviruses. One clone produced β-gal retrovirus with a titer in excess of $10^6$/ml following transfection with pBND8. Two rounds of limiting dilution subcloning were performed subsequently, giving rise to the CAK8, or Bing cell line.

Amphotropic G1Na retroviral supernatant was generated by transient transfection of the CAK8 packaging cell line or of PA317 cells as described in Pear, et al., 1993. Retroviral supernatant was harvested 48 hours post-transfection. VSV-G pseudotyped G1Na retroviral vector (provided by Dr. Elio Vanin, St. Jude Children's Research Hospital, Memphis, Tenn.) was prepared from a stable mouse cell line (gp7C) containing a VSV-G envelope under a tetracycline inducible promoter and an ecotropic gag/pol.

GP7C (Genetic Therapy, Inc., Gaithersburg, Md.), a cell line that constituitively expresses the gag and pol encoded components of the Moloney MuLV under the control of the SV40 early promoter was derived by introducing the plasmid, pM2-SVGP, into thymidine kinase deficient (TK$^-$) 3T3 cells (ATCC, Rockville, Md.) (Russel, et al., *Human Gene Therapy,* Vol. 6, pgs. 635–641 (1995)) by co-transfection with pHR5, a plasmid containing a transcription cassette that confers resistance to hygromycin (Rhee, et al., *J. Virol.,* Vol. 64, pgs. 3844–3852 (1990)). The construction of pM2-SVGP required multiple steps. Initially a 5131bp.PstI-ScaI fragment from pMLV-K (Miller, et al., *J. Virol.,* Vol. 49, pgs. 214–222 (1984)), containing the entire pol gene and the majority of the gag gene, was inserted into pUC18 to give pUC-ΔGP. pUC-GP, which also contains the 5' end of the gag gene, together with a consensus Kozak sequence (Kozak, *J. Mol. Biol.,* Vol. 196, pgs. 947–950 (1987)) was constructed by inserting a 141 bp sequence (using 4 overlapping oligos) into the PstI site of pUC-ΔGP. The entire gag/pol coding region from pUC-GP then was inserted into the SnaBI site of pMET2-PA as a blunted EcoRI fragment and the SV40 promoter from LNSX (Miller, et al., *Biotechniques,* Vol. 7, pgs. 980–990, (1989)), as a blunted BamHI-HindIII fragment, was then cloned into the NotI (blunted) site to give pM2-SVGP.

A retroviral vector genome containing the neo$^R$ gene (G1Na) was introduced into GP7C cells by exposure to culture medium from a producer clone (G1Na.40, Genetic Therapy, Inc., Gaithersburg, Md.) generating amphotropic vector particles. (G1Na.40 was generated by transducing the PA317 cell line with pG1Na). Individual clones were isolated by G418 selection and culture media from each was assayed for content of vector RNA by RNA slot blot analysis. A clone designated GP7CN having the highest apparent titer, was selected.

The first step in deriving cells inducibly expressing VSV-G, using components of the tetracycline resistance operon, was the co-transfection of GP7CN cells with pUHD15-1, which contains the chimeric tet$^R$/VP16 transactivator coding sequences under the control of the CMV1A promoter (Gossen, et al., *Proc. Nat. Acad. Sci.,* Vol. 89, pgs. 5547–5551 (1992)), and pUHD-puro2.pUHD-puro2 was constructed by inserting the 630 bp ClaI-HindIII fragment from pJ6Ωpuro (Morgenstern, et al., *Nuc. Acids Res.,* Vol. 18, pgs. 3587–3596 (1990)) into pIC2OR (Marsh, et al., *Gene,* Vol. 32, pgs. 481–485 (1984)), thereby flanking the puro$^R$ gene with EcoRI sites. The EcoRI fragment containing the puro$^R$ gene then was ligated into pUHD1OS (Fornerod, et al., *Oncogene,* Vol. 10, pgs. 1739–1748 (1995)) to give pUHD-puro1. pUHD-puro1 contains an SphI site which includes the ATG trinucleotide as part of its recognition sequence, immediately 5' to the puro$^R$ gene. The SphI site was removed by partial digestion with SalI, followed by complete digestion with HindIII, blunting of the sites and religation to form pUHD-puro2.

Several clones were isolated and further screened for inducible function of the tet$^R$/VP16 sequence in a transient assay following transfection with a plasmid containing the β-galactosidase coding sequences under the control of the tet° minimal promoter, ptet°-LacZ. ptet°LacZ was constructed by inserting the 439 bp XhoI-SacII fragment from pUHD10-3, which contains the heptameric tet° sequences and the CMV1A promoter (Gossen, et al., 1992) upstream of the LacZ gene in p610ZA (Kothary, et al., *Oxford Surveys on Eukaryotic Genes,* Maclean, ed; Vol. 6, pgs. 145–178 (1989)). A clone designated GP7CN-tTA that exhibited low β-galactosidase activity on assay of lysate from cells incubated with tetracycline and high levels in lysate of cells incubated without tetracycline was selected.

GP7CN-tTA cells then were co-transfected with pUHD10-G and pTK5-109. pUHD10-G was constructed by inserting a 1,665 bp EcoRI fragment containing the VSV-G coding sequences into pUHD-10S (Fornerod, et al. 1995). pTK5-109 was constructed by inserting the coding sequences for thymidine kinase (McKnight, *Nucleic Acids Res.,* Vol. 8, pgs. 5949–5964 (1980)) into a plasmid containing the Herpes Simplex Virus promoter for this gene. The thymidine kinase marker was used for selection. Individual clones then were isolated in medium containing tetracycline (10 μg/ml). Seventy-two hours after removal of the tetracycline, cell lysates were prepared from each clone and screened for inducible VSV-G expression by Western blot analysis. A clone was selected that exhibited high expression.

For the complement inactivation studies, the following sera were employed:

1. Human serum;
2. Heat inactivated human serum, wherein heat inactivation was accomplished by incubation at 55° C. for 30 minutes; and
3. Fetal bovine serum (Bio Whittaker lot no. 4M0454), heat inactivated by incubation at 55° C. for 30 minutes.

Retroviral supernatants then were mixed with each of the above-mentioned serum samples at a relative ratio of 1:10 and incubated for 30 minutes at 37° C. A control sample of each supernatant, to which no serum was added, was kept on ice. A 100 μl sample then is removed from each mixture of retroviral supernatant and serum, and added directly to 10 ml of DMEM (Bio Whittaker) containing 10% heat-inactivated fetal bovine serum (D10) and supplemented with 8 μg/ml Polybrene. ($10^{-3}$ dilution). Each of the resulting samples then is diluted serially to $10^{-5}$ in the above-mentioned medium plus Polybrene. Each of the diluted samples then was plated directly onto a subconfluent monolayer of NIH 3T3TK- cells. 24 hours post-infection, the virus supernatant was removed and replaced with D10 containing G418 (0.8 mg/ml). Colony forming units (CFU's) were counted 7 days post-infection.

Figure 10:
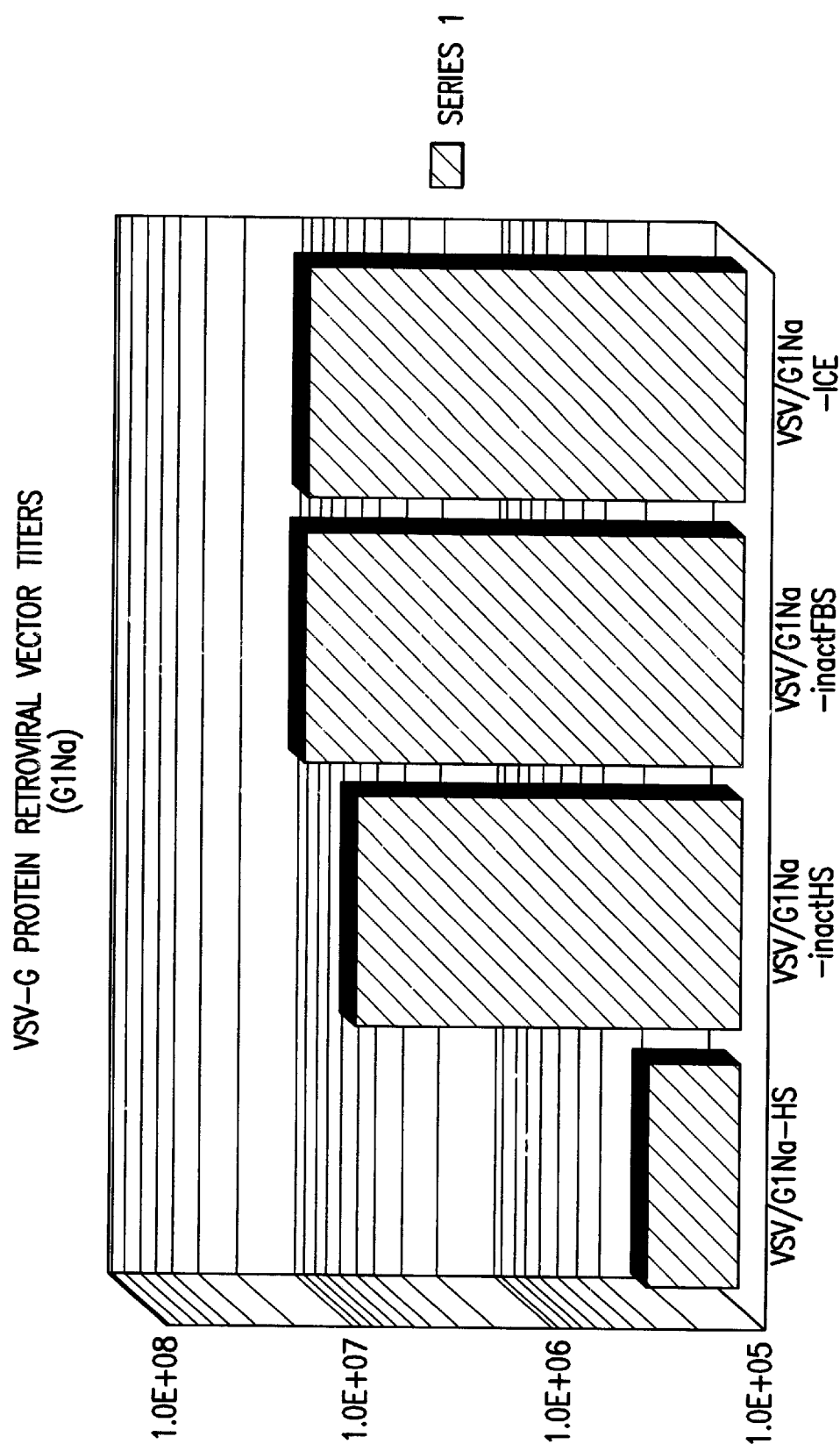
FIG. 10 is a graph of titers of retroviral vectors having a VSV-G retroviral envelope wherein said viruses were produced by a gp7C-derived mouse cell line, upon exposure to human serum or inactivated fetal bovine serum.

As shown in FIG. 10, when the VSV-G pseudotyped G1Na retroviral vector was incubated with human serum for 30 minutes, a 35-fold decrease in titer was observed. No titer loss was seen with heat-inactivated fetal bovine serum, and a minimal loss of titer (approximately 2-fold) was observed with heat-inactivated human serum.

Figure 11:
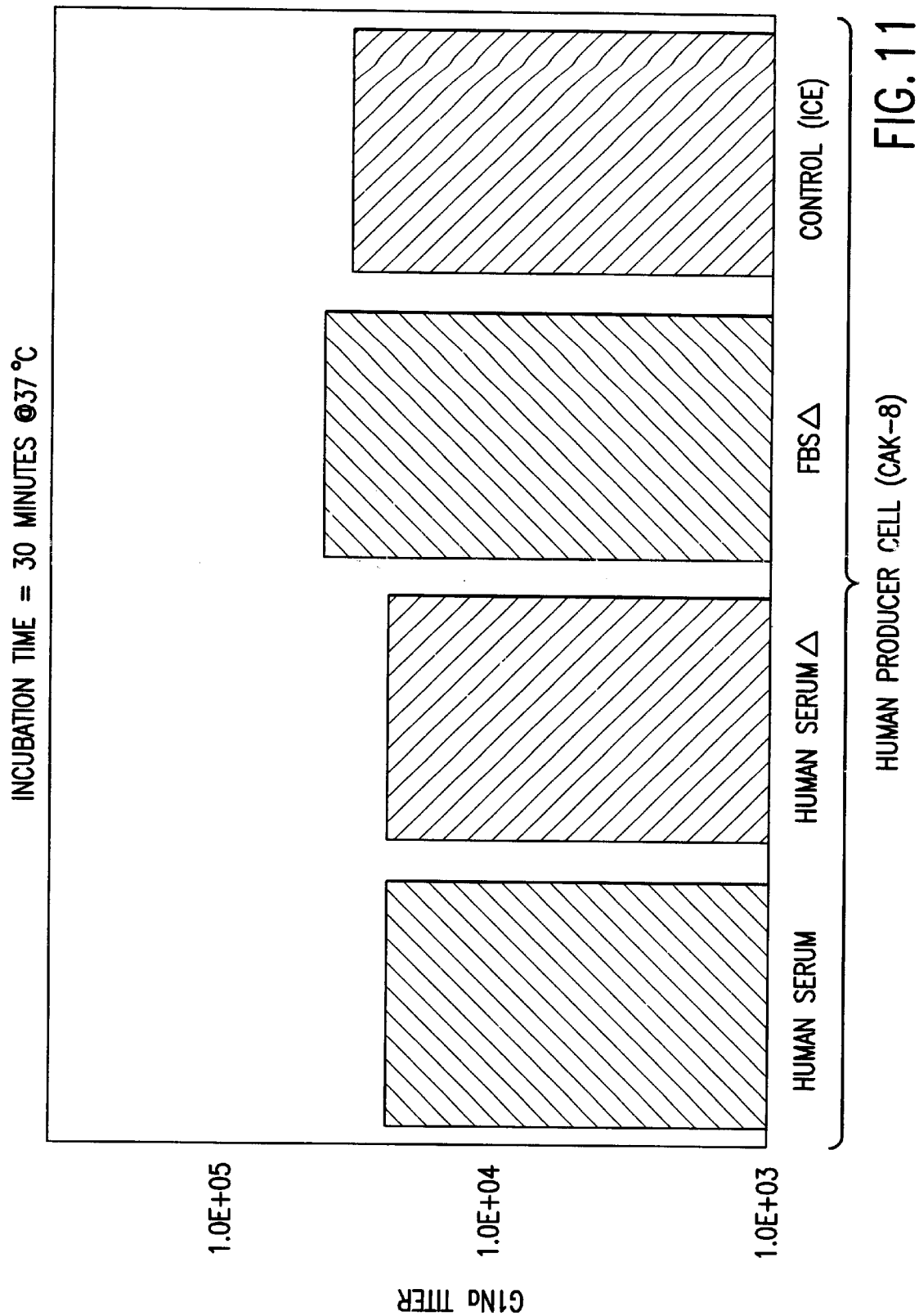
FIG. 11 is a graph of titers of retroviral vectors produced by the CAK8 cell line, upon exposure to human serum or inactivated fetal bovine serum.
Figure 12:
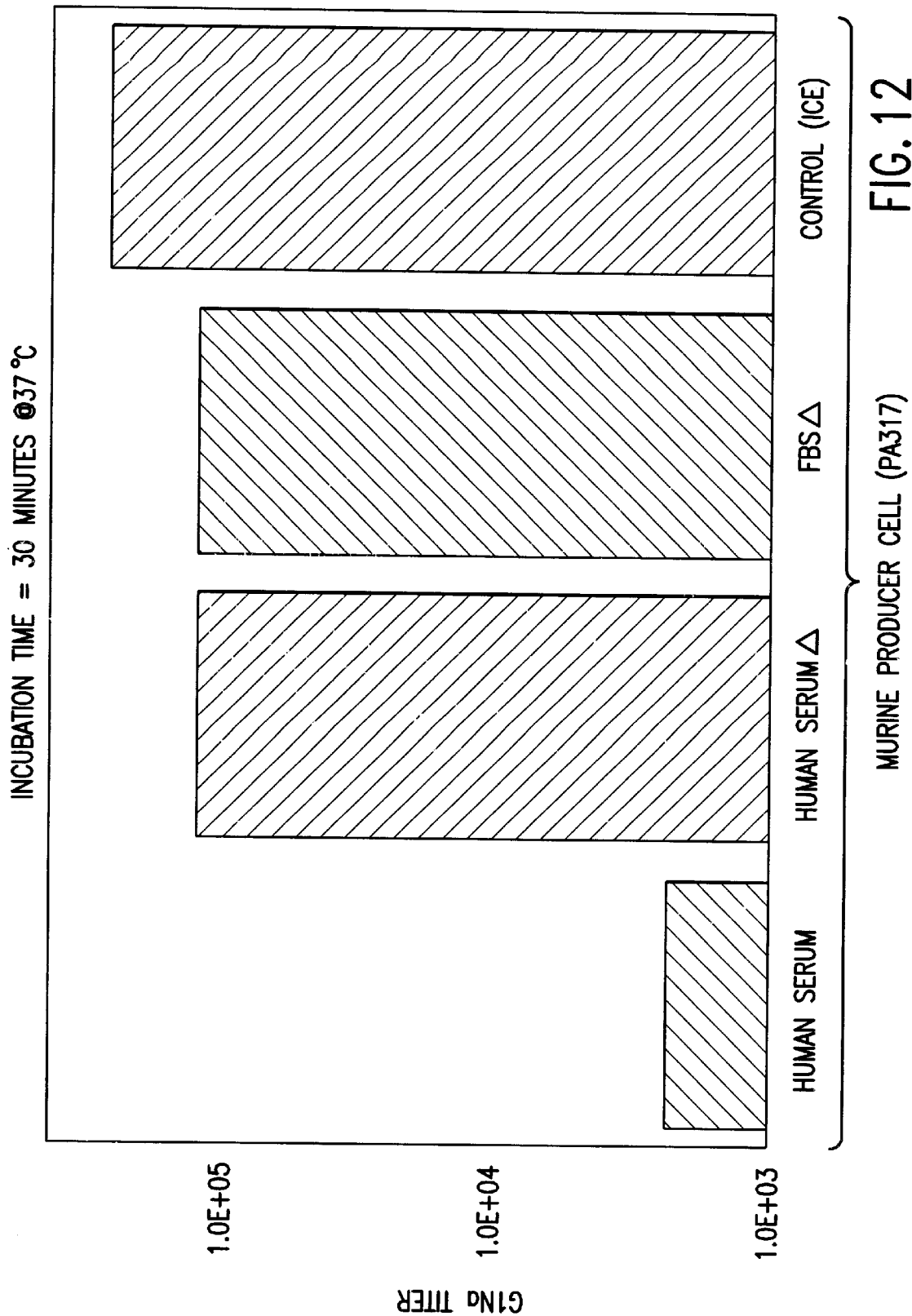
FIG. 12 is a graph of the titers of retroviral vectors produced by the PA317 cell line, upon exposure to human serum or inactivated fetal bovine serum.

In contrast to the results obtained with the VSV-G pseudotyped retroviral vector, amphotropic G1Na vector produced from the CAK8 cell line was completely stable in the presence of human serum (FIG. 11), whereas the G1Na vector produced from PA317 cells resulted in a 50-fold loss in titer after incubation with human serum for 30 minutes (FIG. 12).

Figure 14:
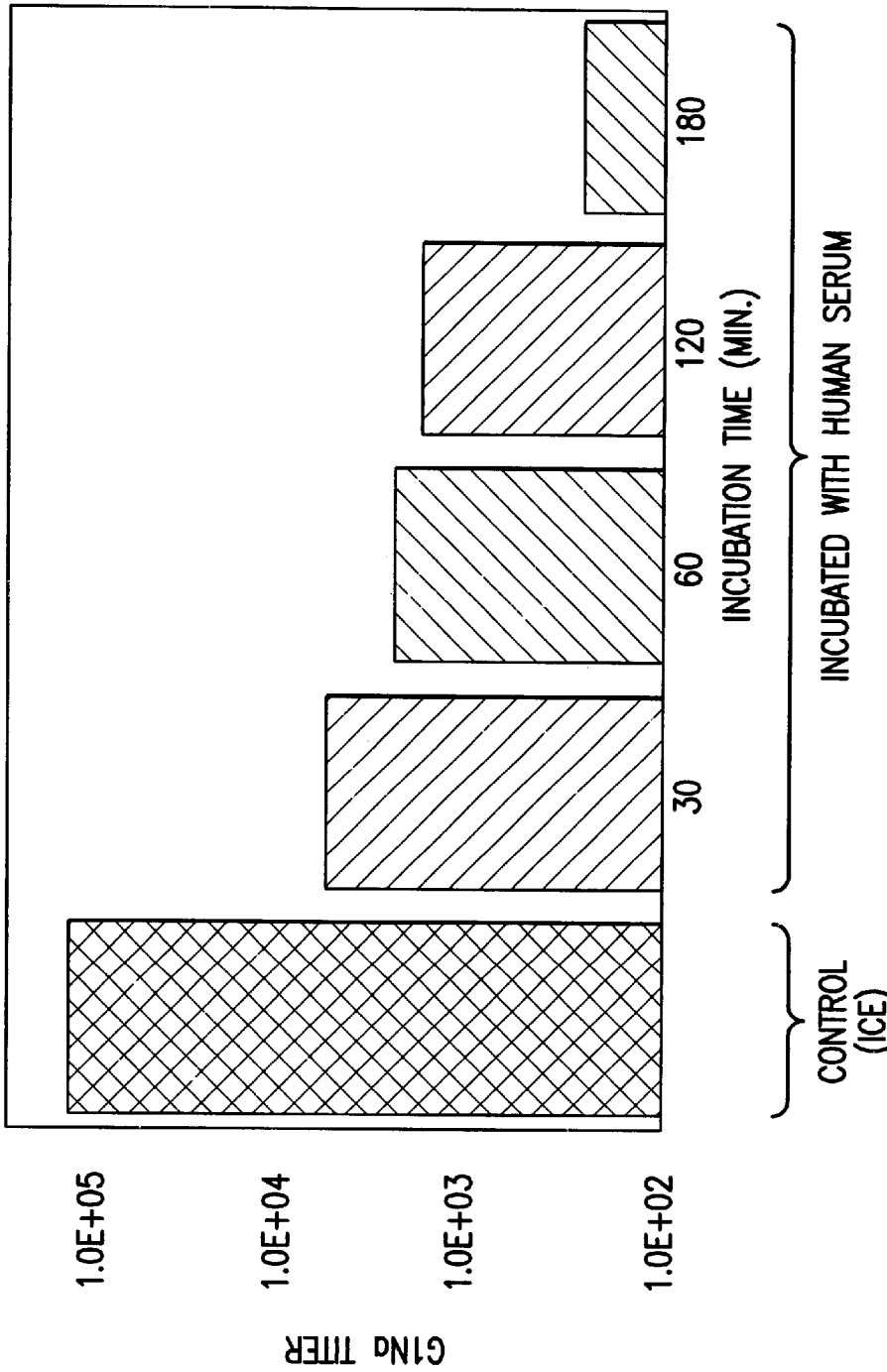
FIG. 14 is a graph of the titers of retroviral vectors produced by the PA317 cell line, upon exposure to human serum for periods of time up to 180 minutes.

As shown in FIG. 14, within 30 minutes of incubation, there is a 40-fold loss of titer of PA317-derived G1Na retrovirus in the presence of human serum. After two hours of incubation, there is a 77-fold decrease in titer.

The disclosure of all patents, publications (including published patent applications), and database accession numbers and depository accession numbers referenced in this specification are specifically incorporated herein by reference in their entirety to the same extent as if each such individual patent, publication, and database accession numbers and depository accession numbers were specifically and individually indicated to be incorporated by reference.

It is to be understood, however, that the scope of the present invention is not to be limited to the specific embodiments described above. The invention may be practiced other than as particularly described and still be within the scope of the accompanying claims.

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 51 bases
      (B) TYPE: nucleic acid
      (C) STRANDEDNESS: single
      (D) TOPOLOGY: linear (ii) MOLECULE TYPE: plasmid DNA (ix) FEATURE:
      (A) NAME/KEY:  Multiple cloning site (xi) SEQUENCE DESCRIPTION: SEQ ID NO: 1:

AATTCGCGGC CGCTACGTAG TCGTAGGATC CCTCGAGAAG CTTGGGCCCA T      51

Example 10

Retroviral supernatants and human serum samples were mixed at a relative ratio of 1:10 and incubated at 37° C. as described in Example 9. A control sample of each supernatant was not mixed with serum and kept on ice. At 30 minutes, 60 minutes, 120 minutes, and 180 minutes, a 100 μl sample was removed and added directly to 10 ml of DMEM containing 10% heat-inactivated fetal bovine serum (D10) and supplemented with 8 μg/ml Polybrene. Each time point sample then was diluted serially to $10^{-5}$ in the above-mentioned medium and Polybrene, and directly plated onto a subconfluent monolayer of NIH 3T3TK- cells. 24 hours post-infection, virus supernatant was removed and replaced with D10 containing G418. CFU's were counted 7 days post-infection.

Figure 13:
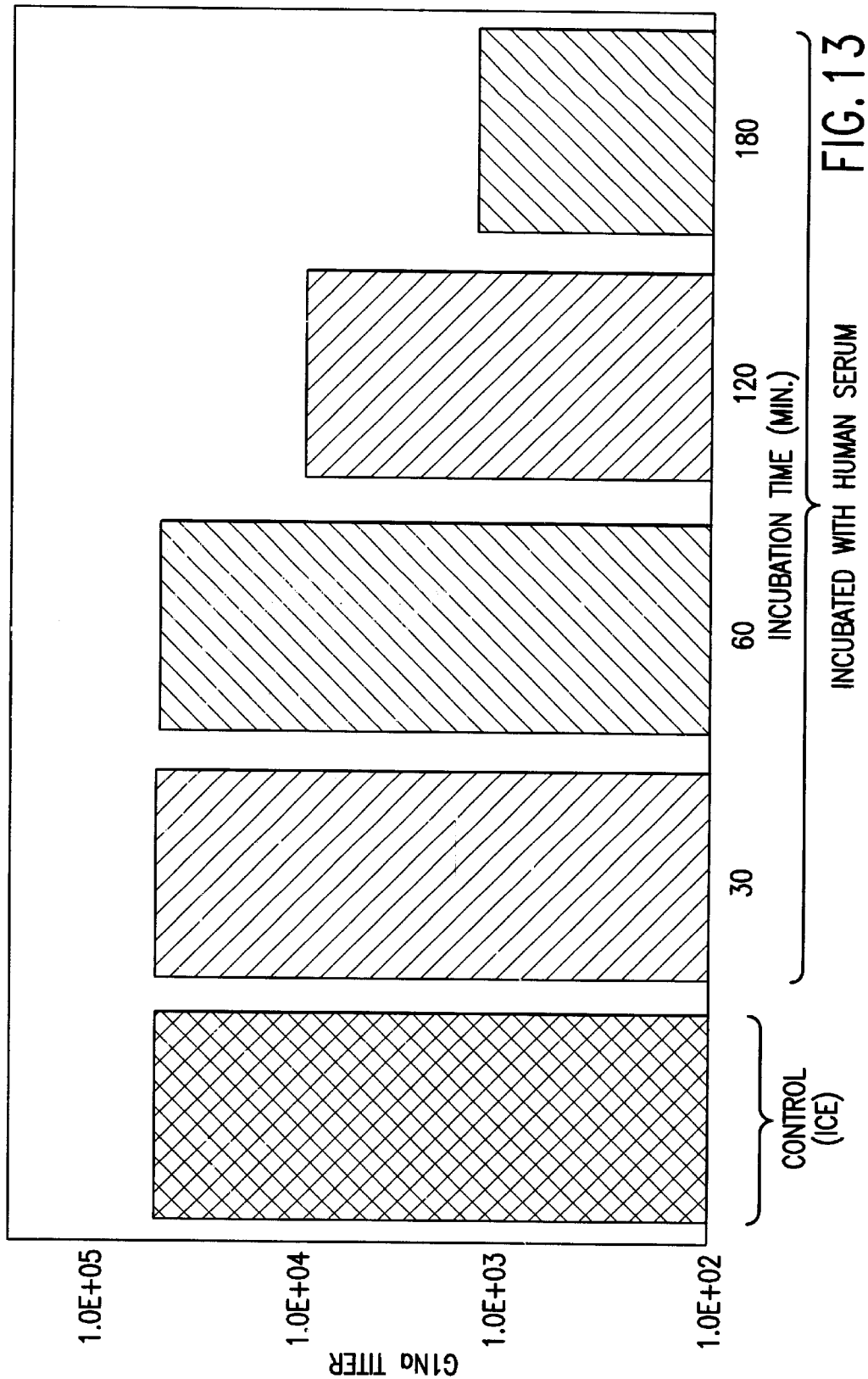
FIG. 13 is a graph of the titers of retroviral vectors produced by the CAK8 cell line, upon exposure to human serum for periods of time up to 180 minutes.

As shown in FIG. 13, amphotropic G1Na vector produced from the CAK8 cell line is stable in the presence of human serum up to 1 hour followed by a 3.5-fold loss of titer after 2 hours.

What is claimed is:

1. A retroviral vector resistant to inactivation by human serum, said retroviral vector having been produced by a producer cell resistant to lysis by human serum, wherein said producer cell includes:

(i) a polynucleotide encoding a retroviral envelope protein, said polynucleotide encoding said envelope protein being obtained from a virus selected from the group consisting of feline endogenous virus RD114, BaEV, SSAV, FeLV-B, NZB virus, avian leukosis virus, and HVJ virus, and (ii) a retroviral vector including a 5' LTR, a 3' LTR, a packaging signal, and at least one polynucleotide encoding a protein or polypeptide of interest, wherein said producer cell does not include the entire viral RNA of feline endogenous virus RD114, BaEV, SSAV, FeLV- B, NZB virus, avian leukosis virus, or HVS virus, and wherein said producer cell is derived from a cell selected from the group consisting of the TE671, HT1080, MV-1-Lu, and human 293 cell lines, and cell lines derived from the TE671, HT1080, Mv-1-Lu, and human 293 lines.

2. The retroviral vector of claim 1, wherein said envelope protein is obtained from feline endogenous virus RD114.

3. The retroviral vector of claim 1, wherein said envelope protein is obtained from BaEV.

4. The retroviral vector of claim 1, wherein said envelope protein is obtained from SSAV.

5. The retroviral vector of claim 1, wherein said envelope protein is obtained from FeLV-B.

6. The retroviral vector of claim 1, wherein said envelope protein is obtained from NZB virus.

7. The retroviral vector of claim 1, wherein said envelope protein is obtained from avian leukosis virus.

8. The retroviral vector of claim 1, wherein said envelope protein is obtained from HVJ virus.

* * * * *